United States Patent [19]

Demerson et al.

[11] 4,070,371

[45] * Jan. 24, 1978

[54] DERIVATIVES OF 1,3,4,9-TETRAHYDROPYRANO[3,4-b]INDOLE-1-ACETIC ACID

[75] Inventors: Christopher A. Demerson, Montreal; Leslie G. Humber; Thomas A. Dobson, both of Dollard des Ormeaux; Ivo L. Jirkovsky, Montreal, all of Canada

[73] Assignee: American Home Products Corporation, New York, N.Y.

[*] Notice: The portion of the term of this patent subsequent to Feb. 17, 1993, has been disclaimed.

[21] Appl. No.: 749,631

[22] Filed: Dec. 13, 1976

Related U.S. Application Data

[60] Division of Ser. No. 555,506, March 5, 1976, Pat. No. 4,012,417, which is a continuation-in-part of Ser. No. 513,693, Oct. 10, 1974, Pat. No. 3,974,179, which is a continuation-in-part of Ser. No. 311,023, Nov. 30, 1972, abandoned, which is a continuation-in-part of Ser. No. 289,714, Sept. 15, 1972, Pat. No. 3,939,178, which is a continuation-in-part of Ser. No. 148,895, June 1, 1971, Pat. No. 3,843,681.

[30] Foreign Application Priority Data

May 16, 1972 South Africa ................ 72/3344

[51] Int. Cl.$^2$ ............................................ C07D 491/04
[52] U.S. Cl. ................................................ 260/326.29
[58] Field of Search .................... 260/326.29, 326.28, 260/326.55 A, 326.9

[56] References Cited

U.S. PATENT DOCUMENTS 3,939,178  2/1976  Demerson et al. ............. 260/326.28

Primary Examiner—Donald G. Daus
Assistant Examiner—David E. Wheeler
Attorney, Agent, or Firm—Stephen Venetianer

[57] ABSTRACT

Indole derivatives characterized by having a 1,3,4,9-tetrahydropyrano[3,4-b]indole or 1,3,4,9-tetrahydrothiopyrano[3,4-b]indole nucleus bearing a substituent in position 1, said substituent incorporating an acid, ester or amide function therein, are disclosed. The nucleus is further substituted at position 1 and may be optionally substituted at positions 3, 4, 5, 6, 7, 8, and 9. The derivatives are useful antiinflammatory, analgesic, antibacterial and antifungal agents and methods for their preparation and use are also disclosed.

21 Claims, No Drawings

DERIVATIVES OF 1,3,4,9-TETRAHYDROPYRANO[3,4-b]INDOLE-1-ACETIC ACID

This is a division, of application Ser. No. 555,506, filed Mar. 5, 1976 and now U.S. Pat. No. 4,012,417, which is a continuation-in-part of Ser. No. 513,693 filed Oct. 10, 1974 which is now U.S. Pat. No. 3,974,179, which is a continuation-in-part of Ser. No. 311,023 filed Nov. 30, 1972 and now abandoned, which is a continuation-in-part of Ser. No. 289,714 filed Sept. 15, 1972 which is now U.S. Pat. No. 3,939,178, which is a continuation-in-part of Ser. No. 148,895 filed June 1, 1971 and now U.S. Pat. No. 3,843,681.

BACKGROUND OF THE INVENTION

This invention relates to novel indole derivatives, to processes for their preparation and to intermediates used in these processes.

Notwithstanding the advances made during the last four decades in the development of agents for the treatment of inflammatory conditions, there still remains a need for effective agents without the side effects associated with the therapeutic agents presently used for this purpose.

The indole derivatives of this invention have been found to exhibit interesting and useful pharmacodynamic properties without eliciting undesirable side effects. Notable attributes of this effect are antiinflammatory and analgesic activities. In addition the compounds of this invention exhibit antibacterial and antifungal properties.

SUMMARY OF THE INVENTION

The indole derivatives of this invention are characterized by having a pyrano[3,4-b]indole or thiopyrano[3,4-b]indole nucleus bearing a substituent at position 1, said substituent incorporating an acid, ester or amide function therein. These derivatives may be represented by formula I

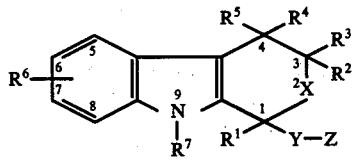

in which $R^1$ is selected from the group consisting of lower alkyl, lower alkenyl, lower alkynyl, lower cycloalkyl, phenyl, benzyl and 2-thienyl, $R^2$, $R^3$, $R^4$ and $R^5$ are the same or different and are each selected from the group consisting of hydrogen and lower alkyl, $R^6$ is selected from the group consisting of hydrogen, lower alkyl, lower cycloalkyl, hydroxy, lower alkoxy, benzyloxy, lower alkanoyloxy, phenyl, nitro, halo, mercapto, lower alkylthio, trifluoromethyl, amino and sulfamoyl, $R^7$ is selected from the group consisting of hydrogen, lower alkyl and lower alkenyl, X is selected from the group consisting of oxy and thio, Y is selected from the group consisting of carbonyl,

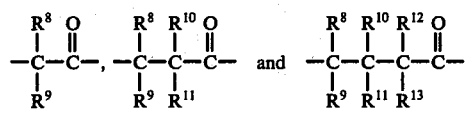

in which each of $R^8$, $R^9$, $R^{10}$, $R^{11}$, $R^{12}$ and $R^{13}$ is hydrogen or lower alkyl, and Z is selected from the group consisting of hydroxy, lower alkoxy, amino, lower alkylamino, di(lower)alkylamino and phenylamino.

Also included within the scope of this invention are pyrano[3,4-b]indole and thiopyrano[3,4-b]indole derivatives of formula I in which $R^6$ represents from one to four substituents, which may be present simultaneously, at positions 5,6,7 and 8 thereof. The exact nature of such substituents does not have to be limited necessarily by the above definitions of $R^6$, and $R^6$ may also include additional definitions, for example, mercapto, lower alkylthio, trifluoromethyl and other halo(lower)alkyls, amino and sulfamoyl, provided that any two such substituents do not interfere with each other. Accordingly, the indole derivatives of this invention are represented also be general formula Ia

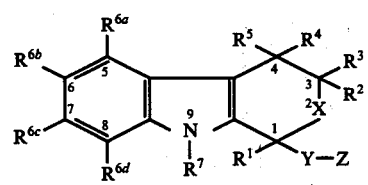

in which $R^1$, $R^2$, $R^3$, $R^4$, $R^5$, $R^7$, X, Y and Z are as defined in the first instance and $R^{6a}$, $R^{6b}$, $R^{6c}$ and $R^{6d}$ are the same or different and each is selected from the group consisting of hydrogen, lower alkyl, lower cycloalkyl, hydroxy, lower alkoxy, benzyloxy, lower alkanoyloxy, phenyl, nitro, halo, mercapto, lower alkylthio, trifluoromethyl, amino and sulfamoyl.

The indole derivatives of this invention of formula I are prepared by reacting a compound of the formula

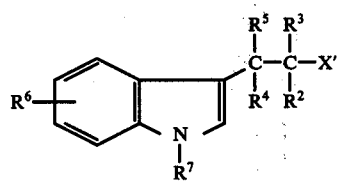

in which $R^2$, $R^3$, $R^4$, $R^5$, $R^6$ and $R^7$ are as defined in the first instance and X' is hydroxy or mercapto with a compound of formula

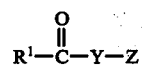

in which $R^1$, Y and Z are as defined in the first instance, in the presence of an acid catalyst.

DETAILED DESCRIPTION OF THE INVENTION

The term "lower alkyl" as used herein contemplates both straight and branched chain alkyl radicals containing from one to six carbon atoms and includes methyl, ethyl, propyl, isopropyl, butyl, isobutyl, 2-methylpentyl and the like.

The term "lower alkenyl" as used herein contemplates both straight and branched chain alkenyl radicals containing from two to six carbon atoms and includes vinyl, allyl, 1-propenyl, methallyl, 2-ethyl-3-butenyl and the like.

The term "lower alkynyl" as used herein contemplates both straight and branched chain alkynyl radicals containing from two to six carbon atoms and includes ethynyl, propargyl, 1,1-dimethylpropargyl and the like.

The term "lower cycloalkyl" as used herein contemplates saturated cyclic hydrocarbon radicals containing from three to six carbon atoms and includes cyclopropyl, cyclobutyl, cyclopentyl and the like.

The term "lower alkoxy" as used herein contemplates both straight and branched chain alkoxy radicals containing from one to four carbon atoms and includes methoxy, ethoxy, isopropoxy and the like.

The term "lower alkanoyloxy" as used herein contemplates both straight and branched chain alkanoyloxy radicals containing from two to six carbon atoms and includes acetoxy, propionyloxy, hexanoyloxy and the like.

The term "halo" as used herein contemplates halogens and includes fluorine, chlorine, bromine and iodine.

Where the term "lower" is used herein as part of the description of alkylamino and dialkylamino, it contemplates one to six carbon atoms for each alkyl group of such a radical and includes methylamino, n-hexylamino, dimethylamino, diethylamino and the like.

The indole derivatives of formula I in which Z is hydroxy, the acid compounds of this invention, form addition salts with suitable inorganic and organic bases. These salts possess the same activities as the parent acid compound when administered to animals and may be utilized in the same manner. Suitable bases to form these salts include, for example, the hydroxides, lower alkoxides, carbonates and bicarbonates of sodium, potassium, calcium and magnesium, as well as the bases, ammonia, triethylamine, benzylamine and the like. The addition salts thus obtained are the functional equivalents of the parent acid compound in respect to their therapeutic use. Hence, these addition salts are included within the scope of this invention and are limited only by the requirement that the bases employed in forming the salts be pharmaceutically acceptable.

Also included within the scope of this invention are the isomers of the compounds of formula I resulting from the asymmetric centers contained therein.

ANTIINFLAMMATORY AND ANALGESIC ACTIVITY

The useful antiinflammatory and analgesic activities of the indole derivatives of this invention may be demonstrated in standard pharmacologic tests, for example, the tests described by R. A. Turner in "Screening Methods in Pharmacology", Academic Press, New York and London, 1965, pp. 152–163 and pp. 100–117, respectively.

More particularly, the antiinflammatory activity of the compounds of this invention may be readily demonstrated in a modification of the Freund's adjuvant test, the adjuvant induced acute edema test as described by J. R. Boissier, et al., Therapie, 25, 43 (1970). This test is known to correlate well with data derived from clinical results with humans. Boissier et al. have demonstrated this correlation with such clinically active compounds as phenylbutazone, mefenamic acid, indomethacin, aspirin, hydrocortisone and prednisolone.

More particularly exemplified, a substantial antiinflammatory effect for the compounds listed below is demonstrable at oral doses of 100 mg/kg or less in this acute edema test. In this test male rats are treated with the test compound 1 hour before the injection of Freund's adjuvant into the paw (day 0). The rats are then treated with the same dose of the test compound for the next 3 days. The antiinflammatory effect of the test compound is measured by the reduction of pedal inflammation, see Turner cited above, and expressed as a percent inhibition from adjuvant injected control rats on day 3.

| COMPOUND | DAILY DOSE (MG/KG) | PERCENT INHIBITION |
|---|---|---|
| 1-methyl-1,3,4,9-tetrahydropyrano[3,4-b]-indole-1-acetic acid, Example No. 1 | 100 | 30 |
| 1-ethyl-1,3,4,9-tetrahydropyrano[3,4-b]-indole-1-acetic acid, Example No. 15 | 100 | 47 |
| 1-propyl-1,3,4,9-tetrahydropyrano[3,4-b]-indole-1-acetic acid, Example No. 16 | 100 | 40 |
| 8-methyl-1-propyl-1,3,4,9-tetrahydropyrano-[3,4-b]indole-1-acetic acid, Example No. 26 | 100 | 44 |
| 1-butyl-1,3,4,9-tetrahydropyrano[3,4-b]-indole-1-acetic acid, Example No. 25 | 100 | 40 |
| 1-t-butyl-1,3,4,9-tetrahydropyrano[3,4-b]-indole-1-acetic acid, Example No. 24 | 100 | 30 |
| 5-methyl-1-propyl-1,3,4,9-tetrahydropyrano[3,4-b]-indole-1-acetic acid, Example 32 | 100 | 44 |
| 1-ethyl-1,3,4,9-tetrahydrothiopyrano[3,4-b]indole-1-acetic acid, Example No. 98 | 25 | 32 |

The lack of side effects for the compounds of this invention may be demonstrated by standard acute toxicity tests (see Turner cited above) and by prolonged administration of the compound to warm-blooded animals.

When the present indole derivatives of this invention are employed as antiinflammatory and analgetic agents in warm-blooded animals, e.g., rats, they may be administered orally, alone or in dosage forms, i.e., capsules or tablets, combined with pharmacologically acceptable excipients, such as starch, milk sugar and so forth. They may also be administered orally in the form of solutions in suitable vehicles such as vegetable oils.

The dosage of the indole derivatives of this invention will vary with the particular compound chosen and form of administration. Furthermore, it will vary with the particular host under treatment. Generally, the compounds of this invention are administered at a concentration level that affords protective effects without any deleterious side effects. These antiinflammatorily-analgesically effective concentration levels are usually obtained within a therapeutic range of 1.0 mg to 500 mg/kg per day, with a preferred range of 10 to 100 mg/kg per day.

ANTIBACTERIAL AND ANTIFUNGAL ACTIVITY

The indole derivatives of this invention also exhibit utility as antibacterial agents against a number of gram-positive and gram-negative microorganisms, such as, *Staphylococcus pyogenes*, both penicillin sensitive and penicillin resistent, *Streptococcus faecalis*, *Escherichia coli*, *Aerobacter aerogenes*, *Salmonella pullorum*, *Pseudomonas aerugenosa*, *Proteus mirabilis*, *Proteus vulgaris*, *Klebsiella pneumoniae* and *Serratia marcescens* and as antifungal agents against a number of pathogenic fungi such as, *Candida albicans*, *Microsporum gypseum* and *Trichophyton granulosum*, in standard tests for antibacterial and antifungal activity, such as those described in "Antiseptics, Disinfectants, Fungicides and Sterilization", G. F. Reddish, Ed., 2nd ed., Lea and Febiger, Philadelphia, 1957 or by D. C. Grove and W. A. Randall in "Assay Methods of Antibiotics", Med. Encycl. Inc., New York 1955.

For example, by employing a test like the serial broth dilution test, see Grove and Randall, cited above, in which dilutions of the compounds of this invention in nutrient broth are inoculated with the microorganisms or fungi, described above, incubated at 37° C. for 2 days, respectively, and examined for the presence of growth, it may be shown that 1-methyl-1,3,4,9-tetrahydropyrano[3,4-b]indole-1-propionic acid is able to inhibit growth totally in this system of *Proteus vulgaris*, *Klebsiella pneumoniae* and *Serratia marcescens* at a concentration of 100 mcg/ml. or less.

When the compounds of this invention are employed as antibiotic or antifungal agents in warm-blooded animals, e.g. rats, they may be administered alone or in combination with pharmacologically acceptable carriers. The proportion of the compound is determined by the solubility and chemical nature of the compound, chosen route of administration and standard biological practice. For example, they may be administered orally in solid form containing such excipients as starch, milk sugar, certain types of clay and so forth. They may also be administered orally in the form of solutions or they may be injected parenterally. For parenteral administration they may be used in the form of a sterile solution containing other solutes, for example, enough saline or glucose to make the solution isotonic.

The dosage of the present therapeutic agents as antibiotic or antifungal agents will vary with the form of administration and the particular compound chosen. Furthermore, it will vary with the particular host under treatment. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford antibacterially or antifungally effective results without causing any harmful or deleterious side effects and preferably at a level that is in a range of from about 1.0 mg. to about 1000 mg. per kilo per day, although as aforementioned variations will occur. However, a dosage level that is in the range of from about 10 mg. to about 500 mg. per kilo per day is most desirably employed in order to achieve effective results.

In addition, the agent may be employed topically. For topical application they may be formulated in the form of solutions, creams, or lotions in pharmaceutically acceptable vehicles containing 0.1–5 percent, preferably 2 percent of the agent and may be administered topically to the infected area of the skin.

Also the antibacterial properties of the compounds of this invention may be utilized for washing equipment in hospitals, homes and farms, instruments used in medicine and bacteriology, clothing used in bacteriological laboratories, and floors, walls and ceiling in rooms in which a background free of gram-positive and gram-negative microorganisms, such as those listed above, is desired. When employed in this manner the compounds of this invention may be formulated in a number of compositions comprising the active compound and an inert material. In such compositions, while the compounds of formula I of this invention may be employed in concentrations as low as 500 p.p.m., from a practical point of view, it is desirable to use from about 0.10% by weight, to about 5% by weight or more.

The formulations that may be used to prepare antiseptic wash solutions of the compounds of this invention are varied and may readily be accomplished by standard techniques, see for example, "Remington's Practice of Pharmacy", E. W. Martin et al., Eds., 12th ed., Mack Publishing Company, Easton, Penn., 1961, pp. 1121–1150. In general, the compounds may be made up in stock solutions. They can also be formulated as suspensions in an aqueous vehicle. These make useful mixtures for decontaminating premises. Also, aqueous vehicles containing emulsifying agents, such as sodium lauryl sulfate, and relatively high concentrations, e.g., up to about 5% by weight, of the compounds may be formulated by conventional techniques.

A typical antiseptic preparation useful for disinfecting floors, walls, ceiling, and articles in a contaminated room may be prepared by adding 5 to 25 g. of N,N,1-trimethyl-1,3,4,9-tetrahydropyrano[3,4-b]indole-1-acetamide to a mixture of 150 to 300 g. of polyethylene glycol 1540 and 150 to 300 g. of polyethylene glycol 300. The resulting mixture is stirred while a solution of 1 to 10 g. of sodium lauryl sulfate in 300 to 400 ml. of water is added portionwise. The article to be disinfected is coated or immersed in the preparation for a prolonged time, for example, one hour, and then rinsed with sterile water.

PREPARATION OF INDOLE DERIVATIVES

For the preparation of the indole derivatives of this invention we prefer to use as starting materials the compounds of the general formula II.

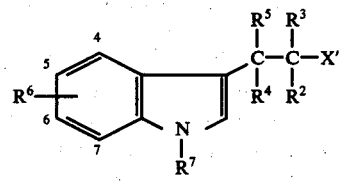

II.

in which $R^2$, $R^3$, $R^4$, $R^5$, $R^6$ and $R^7$ are as defined in the first instance and X' is hydroxy or mercapto.

The starting materials of formula II in which X' is hydroxy are either known, for example, tryptophol, described by H. R. Snyder and F. J. Pilgrim, J. Am.

Chem. Soc. 70, 3770 (1948), or they may be obtained by the following process:

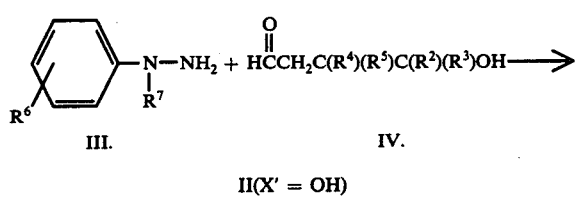

II(X' = OH)

With reference to this process phenylhydrazines of formula III and the hydroxyaldehyde of formula IV are reacted together according to the conditions of the "Fischer Indole Synthesis", for example, see P. L. Julian, E. N. Myer and H. C. Printy, "Heterocylic Compounds", R. C. Elderfield, Ed., Vol. 3, John Wiley and Sons, Inc., New York, 1952, pp. 8–11, to form the desired starting material (II, X' = OH).

The phenylhydrazines of formula III are either known or may be prepared according to known methods. A convenient method involves the diazotization of the appropriately substituted aniline to give the corresponding diazo derivative. The latter compound is then reduced with stannous chloride or sodium sulfite to give the corresponding phenylhydrazine, see L. F. Fieser and M. Fieser, "Advanced Organic Chemistry", Reinhold Publishing Corporation, New York, 1961, p. 734.

The hydroxyaldehydes of formula IV are either known, see for example, "Rodd's Chemistry of Carbon Compounds," S. Coffey, Ed., Vol. I d, 2nd ed., Elsevier Publishing Co., Amsterdam, 1965, pp. 44–49, or they may be prepared according to known methods. A convenient method involves reduction of an appropriate lactone of formula

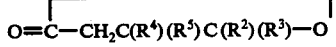

with bis-(3-methyl-2-butyl)borane, H. C. Brown and D. B. Bigley, J. Am. Chem. Soc., 83, 486 (1961), diisobutyl aluminum hydride, L. I. Zakharkkin and I. M. Khorlina, Tetrahedron Letters, 619 (1962) or sodium aluminum hydride, L. I. Zakharkin et al., Tetrahedron Letters, 2087 (1963). The appropriate lactones utilized in this reduction are either commercially available, for example, δ-valerolactone, α-methyl-butyrolactone, or they are described with a variety of methods for their preparation in organic chemistry textbooks; such as the textbooks, "Methoden der Organischen Chemie", Houben-Weyl, E. Muller, Ed., Vol. VI/2, Georg Thieme Verlag, Stuttgart, 1963, pp. 561–852 or L. F. Fieser and M. Fieser, "Advanced Organic Chemistry", cited above.

Alternatively, the starting materials of formula II in which $R^2$, $R^3$, $R^4$ and $R^7$ are hydrogen and X' is hydroxy may be prepared by lithium aluminum hydride reduction, N. G. Gaylord, "Reduction with Complex Metal Hydrides", Interscience Publishers, Inc., New York, 1956, pp. 322–370, of compounds of formula V described by T. Y. Shen, U.S. Pat. No. 3,161,654, Dec. 15, 1964:

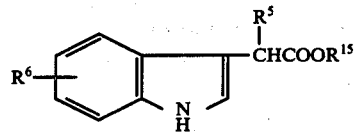

wherein $R^{15}$ is lower alkyl and $R^5$ and $R^6$ are as defined in the first instance.

The starting materials of formula II in which X' is mercapto and $R^2$, $R^3$, $R^4$, $R^5$, $R^6$, and $R^7$ are as defined in the first instance may be obtained by the following process: The appropriate compound of formula II (X' = OH), described above, is treated with phosphorus tribromide in an inert solvent, for example, ether or carbon tetrachloride, to afford the corresponding 3-(2-bromoethyl)indole derivative. The latter compound is then converted to the desired starting material of formula II (X' = SH) by a procedure similar to that described by N. N. Suvorov and V. N. Buyanov, Khim.-Farm. Zh., 1, 4 (1967), [Chem. Abstr. 67, 73474a (1967)], for converting 3-(2-bromoethyl)indole to indole-3-ethanethiol (II; $R^2$, $R^3$, $R^4$, $R^5$, $R^6$ and $R^7$ = H and X' = SH). Accordingly, the appropriate 3-(2-bromoethyl)indole derivative is treated with sodium or potassium thiosulfate to afford the corresponding sodium or potassium β-(3-indolyl)ethyl thiosulfate derivative, respectively, which on treatment with strong alkali for example, sodium or potassium hydroxide, is transformed into the corresponding bis-[ω-(3-indolyl)ethyl]-disulfide derivative. Reduction of the latter compound with lithium aluminum hydride gives the desired compounds of formula II.

It should be noted that the preceding process is not entirely practical for the preparation of the compounds of formula II in which X' is mercapto and $R^6$ is hydroxy or lower alkanoyloxy. For this reason, the preferred starting materials of formula Ii for the ultimate preparation of the compounds of formula I in which $R^6$ is hydroxy or lower alkanoyloxy and X is thio are the corresponding compounds of formula II in which $R^6$ is benzyloxy, readily prepared by this process. When the latter compounds are used as starting materials in this manner, they are first subjected to the process (II + VI → VII), described below. Subsequently, the benzyloxy group is removed by hydrogenation, in the presence of a catalyst, for example, 10% palladium on carbon, to afford the corresponding compound of formula I in which $R^6$ is hydroxy. The latter may be converted if desired to the corresponding compound of formula I in which $R^6$ is lower alkanoyloxy by conventional means, for example, by treatment with the appropriate lower alkanoic anhydride preferably in the presence of pyridine. Likewise, it should be noted that similar use of the starting materials of formula II in which X' is hydroxy and $R^6$ is benzyloxy to obtain the corresponding compound of formula I in which $R^6$ is hydroxy or lower alkanoyloxy is preferred.

For the preparation of the acid and ester compounds of this invention of formula I in which Z is hydroxy or lower alkoxy and $R^1$, $R^2$, $R^3$, $R^4$, $R^5$, $R^6$, $R^7$, X and Y are as defined in the first instance, we have found that the following, hitherto undisclosed process is both practical and convenient:

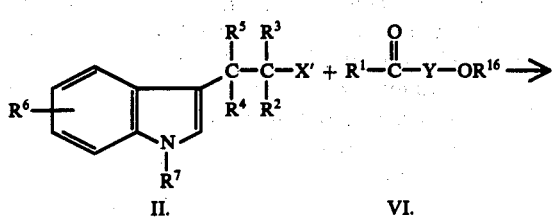

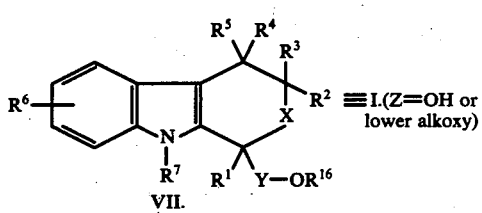

in which $R^1$, $R^2$, $R^3$, $R^4$, $R^5$, $R^6$, $R^7$, X, Y and Z are as defined in this instance, X' is hydroxy or mercapto and $R^{16}$ is hydrogen or lower alkyl. (For convenience and clarity these particular acid and ester compounds of formula I are represented above as formula VII).

With reference to the above scheme the starting material of formula II is condensed with a ketoacid (VI, $R^{16}$ = H) or a ketoester (VI, $R^{16}$ = lower alkyl) in the presence of a suitable acid catalyst to yield the compounds of formula VII.

Generally comparable yields of product are obtained in this process when either the ketoacid or the corresponding ketoester is used. However, in the case where it is desired to prepare acid compounds of formula VII in which Y is

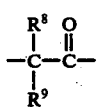

and $R^{16}$ is hydrogen, it is preferable with respect to yield to first condense the appropriate β-ketoester of formula VI rather than the corresponding β-ketoacid and then hydrolyze the resulting ester product to give the desired acid compound.

Moreover, in the general practise of this invention it is often more convenient to prepare the acid compounds of formula VII by using the ketoester instead of the ketoacid in this process and then hydrolyze the resulting ester product to the desired acid, the reason being simply that the ketoesters are generally more readily available either commercially or by synthesis.

The hydrolysis of compounds of formula VII in which $R^{16}$ is lower alkyl to their corresponding acids of formula VII is readily effected by treatment with a suitable alkali, for example, potassium hydroxide or sodium carbonate, in aqueous methanol or aqueous ethanol.

In practising the condensation (II + VI → VII) we have found it preferable to use a solvent as a reaction medium. Any solvent inert to the reaction conditions may be used. Suitable solvents include benzene, toluene, diethyl ether, dioxan, tetrahydrofuran, methylene dichloride, carbon tetrachloride and the like. Benzene and tetrahydrofuran are especially convenient and practical for this use. A variety of suitable acid catalysts may be used for this condensation, for example, the type of catalyst used in a Friedel-Crafts Reaction, i.e. p-toluenesulfonic acid, phosphorus pentoxide, boron trifluoride, zinc chloride, hydrochloric acid and sulfuric acid and the like. p-Toluenesulfonic acid, boron trifluoride and phosphorus pentoxide are included among the preferred acid catalysts. The amount of acid catalyst used is not especially critical and may range from 0.01 molar equivalents to 100 molar equivalents; however, a range of from 0.1 to 10 molar equivalents is generally preferred. The time of the reaction may range from 10 minutes to 60 hours, with the preferred range being from ½ to 24 hours. The temperature of the reaction may range from −20° C. to the boiling point of the reaction mixture. Preferred temperature ranges include 20° to 120° C.

The α-, β-, γ- and δ-ketoacids and -ketoesters of formula VI are either known, for example, ethyl pyruvate, levulinic acid, ethyl α,α-dimethylacetoacetate, β,β-dimethyllevulic acid and benzoylacetic acid or they may be prepared by known methods described in general organic chemistry textbooks. For example, a comprehensive review on the properties and preparation of such α-, β-, γ- and δ-ketoacids and -ketoesters may be found in "Rodd's Chemistry of the Carbon Compounds", cited above, Vol. 1d, pp. 226–274.

Alternatively, the acid compounds of formula I in which Z is hydroxy and $R^1$, $R^2$, $R^3$, $R^4$, $R^5$, $R^6$, $R^7$, X and Y are as defined in the first instance may be prepared by the following process:

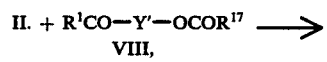

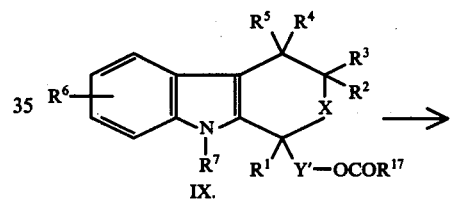

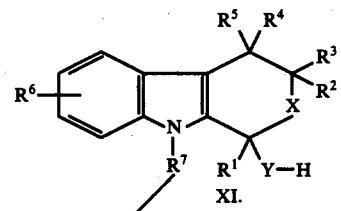

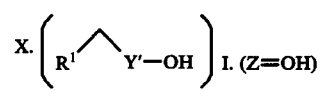

in which Y' is $CH_2$, $C(R^8)(R^9)CH_2$, $C(R^8)(R^9)C(R^{10})R^{11})CH_2$ or $C(R^8)R^9)C(R^{10})(R^{11})C(R^{12})(R^{13})CH_2$, $R^{17}$ is hydrogen or lower alkyl, Z is hydroxy and $R^1$, $R^2$, $R^3$, $R^4$, $R^5$, $R^6$, $R^7$, X and Y are as defined in the first instance.

With reference to this alternative process a starting material of formula II is condensed with an acylated ketoalcohol (VIII) in the presence of a suitable acid catalyst according to the conditions described above for the condensation (II + VI → VII). The ketoalcohol lower alkyl esters are either known, for example, acetonyl acetate of 5-acetoxypentan-2-one, or may be prepared by known methods, for instance, see "Rodd's Chemistry of the Carbon Compounds", cited above, Vol. ld, pp. 49–54. In this manner the condensation product of general formula IX is obtained. Hydrolysis of this product with an aqueous alcoholic solution of a suitable alkali, for example, sodium hydroxide in aqueous methanol, affords the corresponding primary alcohol X. The primary alcohol is then oxidized to the corresponding aldehyde of formula XI. Although a variety of methods are known for the oxidation of a primary alcohol to its corresponding aldehyde, see for example, "Rodd's Chemistry of the Carbon Compounds", cited above, Vol. lc, pp. 4–10, we have found that the method of K. E. Pfitzner and J. G. Moffat, J. Am. Chem. Soc. 87, 5670 (1965) using N,N-dicyclohexylcarbodiimide and dimethyl sulfoxide in the presence of a suitable acid, for example, trifluoroacetic acid, to be both efficacious and convenient in this case. Subsequently the aldehyde XI may be converted to the desired acid compounds of formula I by a variety of oxidizing agents, including silver oxide, alkaline permanganate, hydrogen peroxide, peracids and the like. In this case we prefer to use silver oxide according to the method of M. Delépine and P. Bonnet, Compt. rend., 149,39 (1909).

The amide compound of this invention of formula I in which Z is amino, lower alkylamino, di(lower)alkylamino and phenylamino and $R^1$, $R^2$, $R^3$, $R^4$, $R^5$, $R^6$, $R^7$, X and Y are as defined in the first instance, may be prepared from their corresponding acid compounds of formula I (compounds of formula VII in which $R^{16}$ is hydrogen, described above) by treatment of the latter compounds with a lower alkyl chloroformate, preferably ethyl chloroformate, in the presence of triethylamine, affording the corresponding mixed anhydride, which is converted by treatment with the appropriate amine, such as ammonia, aniline or a suitable alkylamine or dialkylamine, to the desired amide compound of formula I.

Alternatively, these amides of formula I may be prepared from the corresponding esters of the formula I (compounds of formulae VII, in which $R^{16}$ is lower alkyl, described above) by treatment of the latter compounds with the appropriate amine according to known methods, for example, see A. L. J. Beckwith in "The Chemistry of Amides", J. Zalicky, Ed., Interscience Publishers, New York, 1970, pp. 96–105.

Again altenatively, the amide compounds of formula I in which Z is amino, lower alkylamino, di(lower)alkylamino, and phenylamino and $R^1$, $R^2$, $R^3$, $R^4$, $R^5$, $R^6$, $R^7$, X and Y are as defined in the first instance, may be prepared by the condensation of an appropriate starting material of formula II with an appropriate α-, β-, γ- or δ-ketoamide in the presence of a suitable acid catalyst according to the conditions described above for the condensation (II + VI → VII). The ketoamides required for this condensation are either known, for example, pyruvamide or α, α-dimethylacetoacetamide, or they may be prepared by known methods, for instance, see "Rodd's Chemistry of the Carbon Compounds", cited above, Vol. ld, pp. 226–274.

The alkylated acid and ester compounds of this invention of formula I in which $R^7$ is lower alkyl or lower alkenyl and Z is hydroxy or lower alkoxy, are prepared readily from the above described, corresponding acid or ester compounds of formula I in which $R^7$ is hydrogen. This conversion involving the N-alkylation of the indolic nitrogen is effected by treatment of the latter compounds with an appropriate lower alkyl or lower alkenyl halide in an inert solvent in the presence of an acid acceptor. Preferred conditions for effecting this conversion include the use of sodium hydride as an acid acceptor and tetrahydrofuran as the inert solvent.

The N-alkylated amide compounds of formula I in which $R^7$ is lower alkyl or lower alkenyl and Z is amino, lower alkylamino, di(lower)alkylamino or phenylamino are preferably prepared by either treatment of the N-alkylated acid compounds of formula I, described above, with a lower alkyl chloroformate followed by treatment with the appropriate amine, or treatment of the N-alkylated ester compounds of formula I, described above, with an appropriate amine, in the manner described previously for the preparation of the amide compounds of formula I in which $R^7$ is hydrogen.

Finally, it is the intention to cover all changes and modifications of the embodiment of the invention herein chosen for the purpose of disclosure which are within the scope and spirit of this invention. Such changes and modification include those variations which depend on well known interconversions of acids and esters or alternation of the order of N-alkylation in the processes disclosed herein.

For example, in preparing the N-alkylated acid, ester or amide compounds of formula I in which $R^7$ is lower alkyl or lower alkenyl, the changing of the order of the N-alkylation step, as depicted in the embodiment of this invention, by the act of N-alkylation of the starting materials of formula II and subjecting the products thereof to treatment with an appropriate ketoacid or ketoester of formula VI or a ketoamide, according to the teaching of the present disclosure, would not depart from the spirit or scope of this invention.

Likewise, the preparation of the N-alkylated amide compounds of formula I in which $R^7$ is lower alkyl or lower alkenyl and Z is di(lower)alkylamino by N-alkylation of the corresponding compounds of formula I in which $R^7$ is hydrogen, is considered to be a process which would be functionally equivalent to the process embodied herein for the preparation of these compounds.

It will also be apparent to those skilled in the art that the processes taught herein for the preparation of the indole derivatives of formula I are applicable likewise to the preparation of the indole derivatives of formula Ia, described above. In the latter case, the appropriate starting material of formula IIa, see below, prepared analogously to the starting material of formula II, is utilized.

More specifically, the acid and ester compounds of formula Ia in which $R^{6a}$, $R^{6b}$, $R^{6c}$, $R^{6d}$ and $R^7$ are as defined in the first instance, Z is hydroxy or lower alkoxy, and $R^1$, $R^2$, $R^3$, $R^4$, $R^5$, X and Y are as defined in the first instance, are readily prepared by the condensation (IIa + VI → VIIa), illustrated below, according to the conditions described previously for the condensation (II + VI → VII).

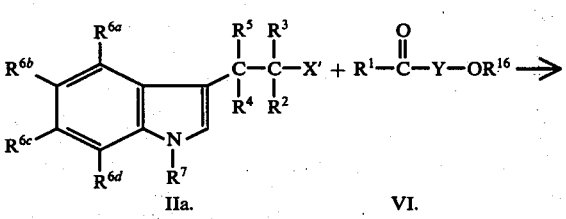

-continued

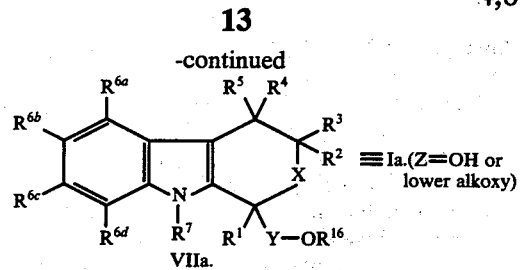

in which $R^1$, $R^2$, $R^3$, $R^4$, $R^5$, $R^{6a}$, $R^{6b}$, $R^{6c}$, $R^{6d}$, $R^7$, X, Y and $R^{16}$ are as defined in the first instance.

Likewise, the acid compounds of formula Ia in which $R^{6a}$, $R^{6b}$, $R^{6c}$, $R^d$ are as defined in the first instance, Z is hydroxy and $R^1$, $R^2$, $R^3$, $R^4$, $R^5$, $R^7$, X and Y are as defined in the first instance may be prepared by the following process:

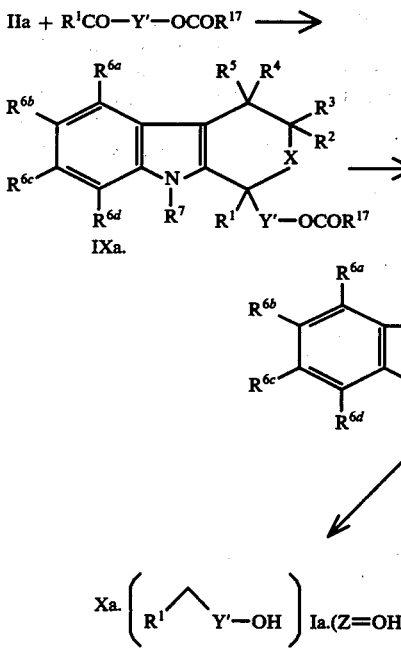

in which $R^1$, $R^2$, $R^3$, $R^4$, $R^5$, X, Y, Y', $R^{6a}$, $R^{6b}$, $R^{6c}$, $R^{6d}$, $R^7$, and $R^{17}$ are as defined in the first instance according to the process disclosed above for the conversion {II + VIII → IX → X → XI → I (Z = OH)}. Subsequent transformation of the above acid and ester compounds of formula Ia to their corresponding N-alkylated and amide derivatives of formula Ia is effected in the same manner for the similar conversions of the acid ester compounds of formula I, described herein.

Alternatively, the amide derivatives of formula Ia are prepared by the condensation of an appropriate starting material of formula IIa with an appropriate α-, β-, γ- or δ-ketoamide in the presence of a suitable acid catalyst according to the conditions described previously for the condensation (II + VI → VII).

The following examples will illustrate further this invention.

EXAMPLE 3

1-Methyl-1,3,4,9-Tetrahydropyrano[3,4-b]Indole-1-Acetic Acid (I; $R^1$ = $CH_3$, $R^2$, $R^3$, $R^4$, $R^5$, $R^6$ And $R^7$ = H, X = O, Y = $CH_2CO$ And Z = OH)

Ethyl acetoacetate (23.4 g., 0.18 moles) is added to a solution of the starting material of formula II, tryptophol (10.0 g., 0.06 moles). in 200 ml. of benzene. After standing for 10 minutes, p-toluenesulfonic acid (1.3 g.) and about 5 g. of hydrated alkali-aluminum silicate (Molecular Sieves No. 4) are added. The mixture is subjected to reflux for thirty minutes, 600 mg. more of p-toluenesulfonic acid is added and refluxing continued for 2½ hours. The molecular sieves are collected and the benzene solution washed successively with 5% sodium bicarbonate and water, dried over sodium sulfate, and evaporated under reduced pressure to dryness affording an oil. The oil is subjected to chromatography on silica gel. Elution with 5% ether in benzene yields the ester, 1-methyl-1,3,4,9-tetrahydropyrano[3,4-b]indole-1-acetic acid ethyl ester, as an oil, γ max/$CHCl_3$ 1715 $cm^{-1}$.

Hydrolysis of this ester to the title compound is effected as follows: The ester is dissolved in 230 ml. of methanol. To this is added 10 g. of KOH in 30 ml. of $H_2O$ and the solution is allowed to stand at room temperature overnight. The methanol is evaporated, water added and the solution washed with benzene. The aqueous phase is acidified with 6N HCl, and extracted with benzene. This organic phase is washed with water, dried over sodium sulfate and evaporated to dryness to give an oil, which is crystallized from benzene containing a trace of petroleum ether to afford the title compound, m.p. 150°-152° C., γ max/$CHCl_3$ 3325 and 1705 $cm^{-1}$.

An equivalent amount of methyl acetoacetate may replace ethyl acetoacetate in the procedure of this Example. In this case, 1-methyl-1,3,4,9-tetrahydropyrano[3,4-b]indole-acetic acid methyl ester, m.p. 87°-90° C. after recrystallization from benzenehexane, is obtained as the ester.

An equivalent amount of propyl acetoacetate may replace ethyl acetoacetate in the procedure of this Example. In this case, 1-methyl-1,3,4,9-tetrahydropyrano[3,4-b]indole-1-acetic acid propyl ester is obtained as the ester.

EXAMPLE 2

1-Methyl-1,3,4,9-Tetrahydropyrano[3,4-b]Indole-1-Propionic Acid (I; $R^1$ = $CH_3$, $R^2$, $R^3$, $R^4$, $R^5$, $R^6$ and $R^7$ = H, X = O, Y = $CH_2CH_2CO$ and Z = OH)

A mixture of the starting material of formula II, Tryptophol (500 mg.), levulinic acid (580 mg.), 75 ml. of benzene, 1.7 g. of phosphorus pentoxide and about 0.5 g. of diatomaceous earth (Celite) is stirred magnetically at room temperature for 15 minutes and then at 70° C. for 1½ hr. The reaction mixture is filtered. The filtrate is washed three times with 5N NaOH; the combined aqueous phase is washed twice with ether and then rendered acidic with cold 50% HCl. The aqueous phase is extracted with chloroform. The chloroform extract is dried ($Na_2SO_4$) and evaporated to dryness. The residue is crystallized from ethyl acetate-petroleum ether to afford the title compound, m.p. 104°-110° C., nmr ($CDCl_3$) δ1.47 (3H), 2.18 (4H), 2.74 (2H), 3.96 (2H), 7.18 (4H), 7.85 (1H), 9.60 (1.H).

The above title compound is also obtained by following the procedure of Example 1 but replacing ethyl acetoacetate with an equivalent amount of ethyl levulinate. In this case 1-methyl-1,3,4,9-tetrahydropyrano[3,4-b]indole-1-propionic acid ethyl ester, m.p. 116°-118° C., $\gamma_{max}^{CHCl_3}$ 1716 $cm^{-1}$, after crystallization from benzene-petroleum ether, is obtained as the ester prior to hydrolysis.

EXAMPLE 3

1-Methyl-1,3,4,9-Tetrahydrothiopyrano[3,4-b]Indole-1-Acetic Acid (I; $R^1$ = $CH_3$, $R^2$, $R^3$, $R^4$, $R^5$, $R^6$ and $R^7$ = H, X = S, Y = $CH_2CO$ and Z = OH)

Indole-3-ethanethiol (1.5 g.) and methyl acetoacetate are mixed with 50 ml. of benzene and the solution heated for 30 min. (bath temperature 70°–80° C.). p-Toluenesulfonic acid (0.15 g.) is added and the reaction mixture is subjected to reflux and stirring for 12 hours. Water formed in the reaction mixture during this period is collected by a water separator. After cooling the benzene solution is washed with a 10% solution of sodium bicarbonate, water, saturated brine and dried over sodium sulfate. Evaporation of the benzene solution yields the ester, 1-methyl-1,3,4,9-tetrahydrothiopyrano[3,4-b]indole-1-acetic acid methyl ester as a semi-solid, $\gamma_{max}^{CHCl_3}$ 1715 cm$^{-1}$.

This ester is then treated with aqueous alcoholic KOH in the manner described for the esters in Example 1 and 2 to afford the title compound, m.p. 147°–149° C., nmr (CDCl$_3$) δ1.86 (S, 3H), 3.06 and 8.12 (6H), 7.35 (multiplet, 4H), 8.71 (1H), 10.31 (1H), after recrystallization from benzene-hexane.

The procedures of Examples 1, or 3 may be followed to prepare other compounds of formula I in which $R^1$, $R^2$, $R^3$, $R^4$, $R^5$, $R^6$, X and Y are as defined in the first instance, $R^7$ is hydrogen and Z is hydroxy. Examples of such compounds of formula I are listed Tables I and II. In each of these examples an equivalent amount of the starting material of formula II listed therein is used instead of the starting material of formula II described in the procedures of Examples 1 and 3. Note that in each of these examples the ester obtained prior to hydrolysis is the corresponding ester compound of formula I in which Z is a lower alkoxy of the product listed therein, the alkyl portion of said lower alkoxy being derived from the $R^{16}$ portion of the ketoester of formula VI employed therein.

Similarly, the procedure of Example 2 may be used to prepare the products listed in Tables I and II. In this case an equivalent amount of the starting material of formula II, listed therein is used instead of the starting material of formula II described in Example 2 and an equivalent amount of the corresponding ketoacid of formula VI of the ketoester of formula VI listed therein is used instead of the said ketoester.

TABLE I

| EXAMPLE | STARTING MATERIAL OF FORMULA II | | | | | | KETOESTER OF FORMULA VI $R^1-\overset{\overset{O}{\|}}{C}-Y-OR^{16}$ | | | PRODUCT: [(PREFIX LISTED BELOW)-1,3,4,9-TETRAHYDROPYRANO-[3,4-b]INDOLE-1-(SUFFIX LISTED BELOW)] |
|---|---|---|---|---|---|---|---|---|---|---|
| | $R^2$ | $R^3$ | $R^4$ | $R^5$ | $R^6$ | X | $R^1$ | Y | $R^{16}$ | PREFIX//SUFFIX |
| 4 | H | H | H | H | H | O | $CH_3$ | CO | $C_2H_5$ | 1-methyl//carboxylic acid |
| 5 | $CH_3$ | H | H | H | H | O | $C_2H_5$ | CO | $C_2H_5$ | 1-ethyl-3-methyl//carboxylic acid |
| 6 | $n-C_3H_7$ | H | H | H | 5-$CH_3$ | O | $n-C_3H_7$ | CO | $CH_3$ | 1,3-diisopropyl-6-methyl//carboxylic acid |
| 7 | $CH_3$ | $CH_3$ | H | H | 5-OH | O | $CH_3CH=CH$ | CO | $CH_3$ | 3,3-dimethyl-6-hydroxy-1-(1-propenyl)//carboxylic acid |
| 8 | H | H | H | H | 7-$C_2H_5$ | O | $HC\equiv C$ | CO | $CH_3$ | 8-ethyl-1-ethynyl//carboxylic acid |
| 9 | H | H | 2-$C_3H_7$ | H | H | O | △ | CO | $CH_3$ | 1-cyclopropyl-4-isopropyl//carboxylic acid |
| 10 | $CH_3$ | H | $C_2H_5$ | H | H | O | (cyclopentyl) | CO | $CH_3$ | 1-cyclopentyl-4,4-diethyl-3,3-dimethyl//carboxylic acid |
| 11 | H | H | H | H | H | O | (phenyl) | CO | $CH_3$ | 1-phenyl//carboxylic acid |
| 12 | $CH_3$ | $C_2H_5$ | H | H | H | O | (benzyl) | CO | $CH_3$ | 1-benzyl-3-ethyl-3-methyl//carboxylic acid |
| 13 | H | H | H | H | 6-Cl | O | (2-methylthienyl) | CO | | 7-chloro-1-(2-thienyl)//carboxylic acid |
| 14 | H | H | $CH_3$ | H | H | O | $CH_3$ | $CH_2CO$ | $C_2H_5$ | 1,4-dimethyl//acetic acid m.p. 163-164° C. |
| 15 | H | H | H | H | H | O | $C_2H_5$ | $CH_2CO$ | $C_2H_5$ | 1-ethyl//acetic acid, m.p. 137-140° C. |
| 16 | H | H | H | H | H | O | $n-C_3H_7$ | $CH_2OO$ | $C_2H_5$ | 1-propyl//acetic acid m.p. 148-151° C. |

| EXAMPLE | STARTING MATERIAL OF FORMULA II | | | | | | KETOESTER OF FORMULA VI ($R^1-CO-Y-OR^{16}$) | | | PRODUCT:[(PREFIX LISTED BELOW)-1,3,4,9-TETRAHYDROPYRANO-[3,4-b]INDOLE-1-(SUFFIX LISTED BELOW)] |
|---|---|---|---|---|---|---|---|---|---|---|
| | $R^2$ | $R^3$ | $R^4$ | $R^5$ | $R^6$ | X | $R^1$ | Y | $R^{16}$ | PREFIX//SUFFIX |
| 17 | H | H | H | H | H | O | $i-C_3H_7$ | $CH_2CO$ | $C_2H_5$ | 1-isopropyl//acetic acid, m.p. 150-152° C. |
| 18 | $CH_3$ | H | H | H | H | O | $CH_2=CHCH_2$ | $CH_2CO$ | $C_2H_5$ | 1-allyl-3-methyl//acetic acid |
| 19 | $CH_3$ | H | H | H | H | O | $n-C_3H_7$ | $CH_2CO$ | $C_2H_5$ | 3-methyl-1-propyl//acetic acid; |

TABLE I-continued

| # | | | | | | | | Notes |
|---|---|---|---|---|---|---|---|---|
| 20 | CH₃ | C₂H₅ | H | CH₃ | H | HC≡C | C₂H₅ | m.p. 75–80° C. (Isomer A), m.p. 146–148° C (Isomer B). 4-ethyl-1-ethynyl-3-methyl//acetic acid, $\nu_{max}$ 3300, 2135, 1710 cm |
| 21 | H | H | H | H | O | CH₃ | C₂H₅ | CH(CH₃)CO α,1'-dimethyl//acetic acid; m.p. 154–156° C. (Isomer A), m.p. 163–165° C. (Isomer B). |
| 22 | H | H | H | H | O | 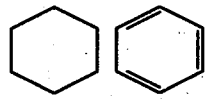 | C₂H₅ | C(CH₃)₂CO 1-cyclohexyl-α,α-dimethyl//acetic acid |
| 23 | H | H | H | H | O | 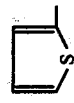 | C₂H₅ | CH₂CO 1-phenyl//acetic acid, m.p. 148–150° C. |
| 24 | H | H | H | H | O | t-C₄H₉ | C₂H₅ | CH₂CO 1-t-butyl//acetic acid, m.p. 210–212° C. |
| 25 | H | H | H | H | O | n-C₄H₉ | C₂H₅ | CH₂CO 1-butyl//acetic acid m.p. 124–127° C. |
| 26 | H | H | H | 7-CH₃ | O | n-C₃H₇ | C₂H₅ | CH₂CO 8-methyl-1-propyl//acetic acid m.p. 127–128° C |
| 27 | H | H | H | H | O | 2-thienyl | C₂H₅ | CH₂CO 1-(2-thienyl)//acetic acid m.p. 127–130° C. |
| 28 | H | H | H | 5-Br | O | C₂H₅ | C₂H₅ | CH₂CO 6-bromo-1-ethyl//acetic acid m.p. 182–184° C. |
| 29 | H | H | H | 5-OCH₃ | O | CH₃ | CH₃ | CH₂CO 6-methoxy-1-methyl//acetic acid, m.p. 142–143° C. |
| 30 | H | H | H | 5-OCOCH₃ | O | CH₃ | C₂H₅ | CH₂CO 6-acetoxy-1-methyl//acetic acid, m.p. 142–143° C. |
| 31 | H | H | H | 5-benzyloxy | O | CH₃ | C₂H₅ | CH₂CO 6-benzyloxy-1-methyl//acetic acid, m.p. 163.5° C. |
| 32 | H | H | H | 4-CH₃ | O | n-C₃H₇ | C₂H₅ | CH₂CO 5-methyl-1-propyl//acetic acid, m.p. 177–178° C. |
| 33 | H | CH₃ | H | 6-CH₃ | O | n-C₃H₇ | C₂H₅ | CH₂CO 7-methyl-1-propyl//acetic acid, m.p. 157–158° C. |
| 34 | H | C₂H₅ | H | 5-NO₂ | O | n-C₃H₇ | C₂H₅ | CH₂CO 6-nitro-1-propyl//acetic acid, m.p. 119–120° C. |
| 35 | i-C₃H₇ | i-C₃H₇ | H | 5-NO₂ | O | CH₂=CH | C₂H₅ | CH(CH₃)CO 3,4-diisopropyl-α-methyl-6-nitro-1-vinyl//acetic acid |
| 36 | H | CH₃ | CH₃ | H | O | n-C₃H₇ | C₂H₅ | CH₂CO 4,4-dimethyl-1-propyl//acetic acid, m.p. 184–185° C. |
| 37 | H | C₂H₅ | H | 7-CH₃ | O | HC≡C | C₂H₅ | C(i-C₃H₇)₂CO α,α-diisopropyl-4-ethyl-1-ethynyl-8-methyl//acetic acid |

TABLE I-continued

| No. | | | | | | | | | Name |
|---|---|---|---|---|---|---|---|---|---|
| 38 | CH₃ | CH₃ | H | 5-OC₂H₅ | O | △ (cyclopropyl) | CH(C₂H₅)CO | C₂H₅ | 1-cyclopropyl-α,α-diethyl-3,3-dimethyl-6-ethoxy//acetic acid |
| 39 | CH₃ | CH₃ | C₂H₅ | C₂H₅ | 6-C₂H₅ | O | cyclohexyl | C(CH₃)₂CO | C₂H₅ | 1-cyclohexyl-α,α,3,3-tetramethyl-4,4,7-triethyl//acetic acid |
| 40 | CH₃ | H | n-C₃H₇ | n-C₃H₇ | 4-n-C₃H₇ | O | phenyl | CH(CH₃)CO | C₂H₅ | α,3-dimethyl-1-phenyl-4,4,5-tripropyl//acetic acid |
| 41 | H | H | H | H | H | O | phenyl | C(CH₃)₂CO | C₂H₅ | α,α-dimethyl-1-phenyl,acetic acid |
| 42 | C₂H₅ | C₂H₅ | C₂H₅ | C₂H₅ | 4-C₂H₅ | O | benzyl (C₆H₅CH₂-) | C(i-C₃H₇)₂CO | C₂H₅ | 1-benzyl-α,α-diisopropyl-3,3,4,4,5-pentaethyl//acetic acid |
| 43 | CH₃ | H | H | H | 7-OCC₂H₅ (C=O) | O | benzyl (C₆H₅CH₂-) | C(CH₃)₂CO | C₂H₅ | 1-benzyl-8-propionoxy-α,α,3-trimethyl//acetic acid |
| 44 | H | H | H | CH₃ | H | O | 2-thienyl | CH(CH₃)CO | C₂H₅ | α,4-dimethyl-1-(2-thienyl)//acetic acid |
| 45 | H | H | H | H | H | O | 2-thienyl, i-C₃H₇ | C(CH₃)₂CO | C₂H₅ | α,α-dimethyl-1-(2-thienyl)//acetic acid |
| 46 | H | H | H | H | 4-I | O | CH₂=CH | CH₂CH₂CO | C₂H₅ | 5-iodo-1-isopropyl//propionic acid |
| 47 | CH₃ | CH₃ | CH₃ | CH₃ | 7-OCCH₃ (C=O) | O | CH₂=CH | CH₂CH(CH₃)CO | C₂H₅ | 8-acetoxy-α,3,3,4,4-pentamethyl-1-vinyl//propionic acid |
| 48 | H | H | H | H | 6-OH | O | HC≡C—CH | C(C₂H₅)₂CH₂— | C₂H₅ | β,β-diethyl-7-hydroxy-1-(2-propynyl)//propionic acid |
| 49 | CH₃ | CH₃ | H | H | 7-NO₂ | O | □ (cyclobutyl) | CH₂CH(n-C₃H₇)—CO | C₂H₅ | 1-cyclobutyl-3-methyl-8-nitro-α-propyl//propionic acid |
| 50 | H | H | CH₃ | CH₃ | 5-CH₃ | O | phenyl | C(CH₃)₂C(CH₃)₂CO | C₂H₅ | α,α,β,β,4,6-hexamethyl-1-phenyl//propionic acid |

TABLE I-continued

| | | | | | | | | |
|---|---|---|---|---|---|---|---|---|
| 51 | i-C$_3$H$_7$ | H | H | H | 7-Br | O | ![benzyl] CH$_2$-C$_6$H$_5$ | CH(CH$_3$)CH(C$_2$H$_5$)CO | C$_2$H$_5$ | 1-benzyl-8-bromo-α-ethyl-3-isopropyl-β-methyl//propionic acid |
| 52 | C$_2$H$_5$ | H | C$_2$H$_5$ | H | 7-Cl | O | 2-methylthienyl | CH$_2$CH$_2$CH$_2$CO | C$_2$H$_5$ | 8-chloro-3,4-diethyl-1-(2-thienyl)//propionic acid |
| 53 | CH$_3$ | H | H | H | H | O | CH$_2$=C(CH$_3$)-CH$_2$ | CH$_2$C(n-C$_3$H$_7$)$_2$CO | C$_2$H$_5$ | 1,3-dimethyl-α,α-dipropyl//propionic acid |
| 54 | CH$_3$ | H | C$_2$H$_5$ | C$_2$H$_5$ | H | O | HC≡C | CH(CH$_3$)C(CH$_3$)$_2$CO | CH$_3$ | 4,4-diethyl-1-methallyl-α,α,β,3-tetramethyl//propionic acid |
| 55 | H | H | CH$_3$ | CH$_3$ | H | O | cyclopentyl | C(CH$_3$)$_2$CH$_2$CO | CH$_3$ | 1-ethynyl-β,β,4,4-tetramethyl//propionic acid |
| 56 | H | H | n-C$_3$H$_7$ | H | 4-OCC$_2$H$_5$ (O=) | O | phenyl | C(C$_2$H$_5$)$_2$C(C$_2$H$_5$)CO | CH$_3$ | 1-cyclopentyl-5-propionoxy-4-propyl-α,β,β-triethyl//propionic acid |
| 57 | n-C$_3$H$_7$ | H | H | H | 4-OCH$_3$ | O | 2-methylbenzyl | CH$_2$CH(CH$_3$)CO | C$_2$H$_5$ | 5-methoxy-α-methyl-1-phenyl-3-propyl//propionic acid |
| 58 | H | H | n-C$_3$H$_7$ | H | 6-benzyloxy | O | 2-methylthienyl | CH$_2$CH(C$_2$H$_5$)CO | C$_2$H$_5$ | 1-benzyl-7-benzyloxy-α-ethyl-4-isopropyl//propionic acid |
| 59 | CH$_3$ | CH$_3$ | CH$_3$ | CH$_3$ | 7-Cl | O | CH$_2$=CHCH$_2$ | CH(CH$_3$)CH$_2$CO | C$_2$H$_5$ | 8-chloro-β,3,3,4,4-pentamethyl-1-(2-thienyl)//propionic acid |
| 60 | C$_2$H$_5$ | H | H | H | 5-NO$_2$ | O | CH$_3$C≡CH | CH(C$_2$H$_5$)$_2$C(C$_2$H$_5$)CO | CH$_3$ | 1-methyl-6-nitro-α,α,β,β,3-pentamethyl//propionic acid |
| 61 | C$_2$H$_5$ | C$_2$H$_5$ | H | H | 5-F | O | cyclopropyl | CH(CH$_3$)CH(CH$_3$)CO | C$_2$H$_5$ | 1-allyl-6-fluoro-α-methyl-β,3,3-triethyl//propionic acid |
| 62 | C$_2$H$_5$ | C$_2$H$_5$ | H | H | 4-C$_2$H$_5$ | O | phenyl | C(n-C$_3$H$_7$)CH$_2$CO | CH$_3$ | 1-propyl-1-(1-propynyl)-3,3,5-triethyl//propionic acid |
| 63 | H | H | H | H | 6-OC$_2$H$_5$ | O | | CH(C$_2$H$_5$)CH(C$_2$H$_5$)CO | C$_2$H$_5$ | 1-cyclopropyl-α,β-diethyl-6-ethoxy//propionic acid |
| 64 | CH$_3$ | CH$_3$ | CH$_3$ | CH$_3$ | 6-O-n-C$_3$H$_7$ | O | | C(CH$_3$)$_2$CH(CH$_3$)CO | C$_2$H$_5$ | α,β,3,3,4,4-heptamethyl-1-phenyl-7-propoxy//propionic acid |

TABLE I-continued

| | | | | | | | | |
|---|---|---|---|---|---|---|---|---|
| 65 | C$_2$H$_5$ | C$_2$H$_5$ | H | H | 5-CH$_3$ | O | [benzyl group] | C(CH$_3$)$_2$C(CH$_3$)$_2$CO | C$_2$H$_5$ | 1-benzyl-3,3-diethyl-α,α,β,β,6-pentamethyl//propionic acid |
| 66 | n-C$_3$H$_7$ | H | H | H | 4-OH | O | [methylthienyl group] | C(CH$_3$)$_2$C(CH$_3$)$_2$CO | C$_2$H$_5$ | 5-hydroxy-3-propyl-α,α,β,β-tetramethyl-1-(2-thienyl)//propionic acid |
| 67 | H | CH$_3$ | H | H | H | O | C$_2$H$_5$ | CH$_2$CH$_2$CO | C$_2$H$_5$ | 1-methyl//butyric acid, m.p. 132–135° C |
| 68 | CH$_3$ | H | H | H | H | O | C$_2$H$_5$ | CH(CH$_3$)CH$_2$CH$_2$CO | C$_2$H$_5$ | γ,3-dimethyl-1-ethyl//butyric acid |
| 69 | CH$_3$ | CH$_3$ | H | H | H | O | n-C$_3$H$_7$ | C(C$_2$H$_5$)$_2$CH$_2$CH$_2$CO | C$_2$H$_5$ | γ,γ-diethyl-3,3-dimethyl-1-propyl//butyric acid |
| 70 | CH$_3$ | CH$_3$ | n-C$_3$H$_7$ | H | H | O | CH$_2$=CH | O(n-C$_3$H$_7$)$_2$CH(n-C$_3$H$_7$)CH$_2$CO | C$_2$H$_5$ | 3,3-dimethyl-β,γ,γ,4-tetrapropyl-1-vinyl//butyric acid |
| 71 | H | H | H | H | H | O | CH$_2$=CHCH$_2$ | [C(CH$_3$)$_2$]$_2$CH$_2$CO | C$_2$H$_5$ | 1-allyl-β,β,γ,γ-tetramethyl//butyric acid |
| 72 | H | H | C$_2$H$_5$ | H | 6-Cl | O | CH$_2$=CH— | [C(C$_2$H$_5$)$_2$]$_2$CH(C$_2$H$_5$)CO | C$_2$H$_5$ | 7-chloro-α,β,β,γ,γ,4-4-heptaethyl-1-vinyl//butyric acid |
| 73 | H | H | CH$_3$ | H | 4-CH$_3$ | O | HC≡CH | [C(CH$_3$)$_2$]$_3$CO | C$_2$H$_5$ | 1-ethynyl-α,α,β,β,γ,γ,4,5-octamethyl//butyric acid |
| 74 | C$_2$H$_5$ | C$_2$H$_5$ | C$_2$H$_5$ | H | 5-OCCH$_3$ (O=) | O | CH$_3$C≡CH | CH(C$_2$H$_5$)[C(C$_2$H$_5$)$_2$]CO | C$_2$H$_5$ | 6-acetoxy-α,α,β,β,γ,3,4-octaethyl-1-(1-propynyl)//butyric acid |
| 75 | H | H | CH$_3$ | CH$_3$ | 7-OCH$_3$ | O | [cyclobutyl] | CH$_2$[C(CH$_3$)$_2$]$_2$CO | C$_2$H$_5$ | 1-cyclobutyl-α,α,β,β,4,4-hexamethyl-8-methoxy//butyric acid |
| 76 | H | H | H | H | 4-Br | O | [cyclopentyl] | CH$_2$CH(CH$_3$)C(CH$_3$)$_2$CO | C$_2$H$_5$ | 5-bromo-1-cyclopentyl-α,α,β-trimethyl//butyric acid |
| 77 | CH$_3$ | CH$_3$ | H | H | 4-n-C$_3$H$_7$ | O | [cyclopropyl] | CH$_2$CH$_2$C(C$_2$H$_5$)$_2$CO | C$_2$H$_5$ | 1-cyclopropyl-α,α-diethyl-3,3-dimethyl-5-propyl//butyric acid |
| 78 | H | H | H | H | 7-C$_2$H$_5$ | O | [phenyl] | CH$_2$CH$_2$CH(CH$_3$)CO | C$_2$H$_5$ | 8-ethyl-α-methyl-1-phenyl//butyric acid |
| 79 | CH$_3$ | CH$_3$ | CH$_3$ | H | 5-F | O | [phenyl] | [CH(CH$_3$)]$_3$CO | C$_2$H$_5$ | 6-fluoro-α,β,γ,3,3,4-hexamethyl-1-phenyl//butyric acid |
| 80 | CH$_3$ | CH$_3$ | H | H | 4-CH$_3$ | O | [phenyl] | CH(C$_2$H$_5$)CH$_2$CH(C$_2$H$_5$)CO | C$_2$H$_5$ | α,γ-diethyl-1-phenyl-3,3,5-trimethyl//butyric acid |

TABLE I-continued

| # | | | | | | | |
|---|---|---|---|---|---|---|---|
| 81 | $C_2H_5$ | H | H | 6-$NO_2$ | O | benzyl (-$CH_2$-$C_6H_5$) | [CH(CH$_3$)]$_3$CO | 1-benzyl-3-ethyl-7-nitro-α,β,γ-trimethyl//butyric acid |
| 82 | $CH_3$ | $CH_3$ | H | 4-n-$C_3H_7$ | O | benzyl | $CH_2[CH(C_2H_5)]_2CO$ | 1-benzyl-α,β-diethyl-3,3-dimethyl-5-propyl//butyric acid |
| 83 | H | H | H | 7-CH | O | benzyl | $C(CH_3)_2CH_2C(CH_3)_2CO$ | 1-benzyl-8-hydroxy-α,α,γ,γ-tetramethyl//butyric acid |
| 84 | $CH_3$ | H | $CH_3$ | 4-$OC_2H_5$ | O | 2-thienyl | [C(CH$_3$)$_2$]$_3$CO | 5-ethoxy-α,α,β,β,γ,γ-3,4-octomethyl-1-(2-thienyl)//butyric acid |
| 85 | $C_2H_5$ | $CH_3$ | $C_2H_5$ | 6-Cl | O | 2-thienyl | $CH_2CH_2C(C_2H_5)_2CO$ | 7-chloro-α,α,3,4,4-pentaethyl-1-(2-thienyl)//butyric acid |
| 86 | $CH_3$ | $CH_3$ | $CH_3$ | 4-Br | O | 2-thienyl | $CH_2CH_2CH(CH_3)CO$ | 5-bromo-α,3,3,4,4-pentamethyl-1-(2-thienyl)//butyric acid |

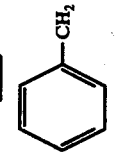

TABLE II-continued

| EXAMPLE | R² | R³ | R⁴ | R⁵ | R⁶ | X | (structure) | Y | | PREFIX//SUFFIX |
|---|---|---|---|---|---|---|---|---|---|---|
| 105 | H | H | H | H | H | S | cyclohexyl | C(CH₃)₂CO | C₂H₅ | 1-cyclohexyl-α,α-dimethyl//acetic acid |
| 106 | H | H | H | H | H | S | phenyl | CH₂CO | C₂H₅ | 1-phenyl//acetic acid |
| 107 | H | H | H | H | H | S | t-C₄H₉ | CH₂CO | C₂H₅ | 1-t-butyl//acetic acid |
| 108 | H | H | H | H | H | S | n-C₄H₉ | CH₂CO | C₂H₅ | 1-butyl//acetic acid |
| 109 | H | H | H | H | 7-CH₃ | S | n-C₃H₇ | CH₂CO | C₂H₅ | 8-methyl-1-propyl//acetic acid |
| 110 | H | H | H | H | H | S | 2-thienyl (5-methyl) | CH₂CO | C₂H₅ | 1-(2-thienyl)//acetic acid |
| 111 | H | H | H | H | 5-Br | S | n-C₃H₇ | CH₂CO | C₂H₅ | 6-bromo-1-propyl//acetic acid |
| 112 | H | H | H | H | 5-OCH₃ | S | CH₃ | CH₂CO | CH₃ | 6-methoxy-1-methyl//acetic acid |

PRODUCT: [(PREFIX LISTED BELOW)-1,3,4,9-TETRAHYDROTHIO-PYRANO[3,4-b]INDOLE-1-SUFFIX LISTED BELOW)

| | STARTING MATERIAL OF FORMULA II | | | | | | KETOESTER OF FORMULA VI (R¹—CO—Y—OR¹⁶) | | | |
|---|---|---|---|---|---|---|---|---|---|---|
| EXAMPLE | R² | R³ | R⁴ | R⁵ | R⁶ | X | R¹ | Y | R¹⁶ | PREFIX//SUFFIX |
| 113 | H | H | H | H | 5-OCOCH₃ | S | CH₃ | CH₂CO | C₂H₅ | 6-acetoxy-1-methyl//acetic acid |
| 114 | H | H | H | H | 5-benzyloxy | S | CH₃ | CH₂CO | C₂H₅ | 6-benzyloxy-1-methyl//acetic acid |
| 115 | H | H | H | H | 4-CH₃ | S | n-C₃H₇ | CH₂CO | C₂H₅ | 5-methyl-1-propyl//acetic acid |
| 116 | H | H | H | H | 6-CH₃ | S | n-C₃H₇ | CH₂CO | C₂H₅ | 7-methyl-1-propyl//acetic acid |
| 117 | H | H | H | H | 7-F | S | CH₂=CH | CH₂CO | C₂H₅ | α,α-diethyl-8-fluoro-1-vinyl//acetic acid |
| 118 | H | H | i-C₃H₇ | H | 5-NO₂ | S | CH₂=CH | CH(CH₃)CO | C₂H₅ | 3,4-diisopropyl-α-methyl-α-nitro-1-vinyl//acetic acid |
| 119 | CH₃ | H | H | H | 5-Cl | S | CH₃C≡C | CH(i-C₃H₇)CO | C₂H₅ | 6-chloro-3,3-dimethyl α-isopropyl-1-(1-propynyl)//acetic acid |
| 120 | H | CH₃ | C₂H₅ | H | 7-CH₃ | S | HC≡C | C(i-C₃H₇)₂CO | C₂H₅ | α,α-diisopropyl-4-ethyl-1-ethynyl-8-methyl//acetic acid |
| 121 | CH₃ | CH₃ | H | H | 5-OC₂H₅ | S | (cyclopropyl) | CH(C₂H₅)CO | C₂H₅ | 1-cyclopropyl-α,α-diethyl-3,3-dimethyl-6-ethoxy//acetic acid |

TABLE II-continued

| | | | | | | | | |
|---|---|---|---|---|---|---|---|---|
| 122 | CH$_3$ | CH$_3$ | C$_2$H$_5$ | 6-C$_2$H$_5$ | S | cyclohexyl | C(CH$_3$)$_2$CO | C$_2$H$_5$ | 1-cyclohexyl-α,α,3,3-tetramethyl-4,4,7-triethyl//acetic acid |
| 123 | CH$_3$ | H | n-C$_3$H$_7$ | 4-n-C$_3$H$_7$ | S | phenyl | CH(CH$_3$)CO | C$_2$H$_5$ | α,3-dimethyl-1-phenyl-4,4,5-triphenyl//acetic acid |
| 124 | H | H | H | H | S | phenyl | C(CH$_3$)$_2$CO | C$_2$H$_5$ | α,α-dimethyl-1-phenyl//acetic acid |
| 125 | C$_2$H$_5$ | C$_2$H$_5$ | C$_2$H$_5$ | 4-C$_2$H$_5$ | S | benzyl | C(i-C$_3$H$_7$)$_2$CO | C$_2$H$_5$ | 1-benzyl-α,α-diisopropyl-3,3,4,4,5-pentaethyl//acetic acid |
| 126 | CH$_3$ | H | H | 7-OCC$_2$H$_5$ (O=) | S | benzyl | C(CH$_3$)$_2$CO | C$_2$H$_5$ | 1-benzyl-8-propionoxy-α,α,3-trimethyl//acetic acid |
| 127 | H | H | H | H | S | 2-thienyl | CH(CH$_3$)CO | C$_2$H$_5$ | α,4-dimethyl-1-(2-thienyl)//acetic acid |
| 128 | H | H | H | H | S | 5-methyl-2-thienyl | C(CH$_3$)$_2$CO | C$_2$H$_5$ | α,α-dimethyl-1-(2-thienyl)//acetic acid |
| 129 | H | H | H | H | S | CH$_2$=CH | CH$_2$CH$_2$CO | C$_2$H$_5$ | 1-methyl//propionic acid |
| 130 | CH$_3$ | CH$_3$ | CH$_3$ | H | S | CH$_2$=CH | CH$_2$CH(CH$_3$)CO | C$_2$H$_5$ | 8-acetoxy-α,3,3,4,4-pentamethyl-1-vinyl//propionic |
| 131 | H | H | H | 7-OCCH$_3$ (O=) | S | HC≡C—CH$_2$ | CH$_2$C(C$_2$H$_5$)$_2$CO | C$_2$H$_5$ | β,β-diethyl-7-hydroxy-1-(2-propynyl)//propionic acid |
| 132 | CH$_3$ | H | H | 6-OH | S | cyclobutyl | CH(n-C$_3$H$_7$)CH$_2$CO | C$_2$H$_5$ | 1-cyclobutyl-3-methyl-8-nitro-α-propyl//propionic acid |
| 133 | H | CH$_3$ | CH$_3$ | 7-NO$_2$ | S | phenyl | C(CH$_3$)$_2$C(CH$_3$)$_2$CO | C$_2$H$_5$ | α,α,β,β,4,6-hexamethyl-1-phenyl//propionic acid |
| 134 | i-C$_3$H$_7$ | H | H | 5-CH$_3$ | S | benzyl | CH(CH$_3$)CH(C$_2$H$_5$)CO | C$_2$H$_5$ | 1-benzyl-8-bromo-α-ethyl-3-isopropyl-β-methyl//propionic acid |

Note: Row 134 has 7-Br substituent.

TABLE II-continued

| | | | | | | | | |
|---|---|---|---|---|---|---|---|---|
| 135 | C₂H₅ | H | C₂H₅ | H | 7-Cl | s | (2-methylthienyl) | CH₂CH₂CH₂CO | C₂H₅ | 8-chloro-3,4-diethyl-1-(2-thienyl)//propionic acid |
| 136 | CH₃ | H | H | H | H | s | (2-methylthienyl) | CH₂C(n-C₃H₇)₂CO | C₂H₅ | 1,3-dimethyl-α,α-dipropyl//propionic acid |
| 137 | CH₃ | H | C₂H₅ | C₂H₅ | H | s | CH₂=C(CH₃)CH₂ | CH(CH₃)C(CH₃)₂CO | CH₃ | 4,4-diethyl-1-methallyl-α,α,β,3-tetramethyl//propionic acid |
| 138 | H | CH₃ | CH₃ | CH₃ | H | s | HC≡C | C(CH₃)₂CH₂CO | CH₃ | 1-ethynyl-β,β,4,4-tetramethyl//propionic acid |
| 139 | H | n-C₃H₇ | H | H | 4-OCC₂H₅ (C=O) | s | cyclopentyl | C(C₂H₅)₂C(C₂H₅)CO | CH₃ | 1-cyclopentyl-5-propionoxy-4-propyl-α,β,β-triethyl//propionic acid |
| 140 | n-C₃H₇ | H | H | H | 4-OCH₃ | s | benzyl | CH₂CH(CH₃)CO | C₂H₅ | 5-methoxy-α-methyl-1-phenyl-3-propyl//propionic acid |
| 141 | H | i-C₃H₇ | H | H | 6-benzyloxy | s | (2-methylthienyl) | CH₂CH(C₂H₅)CO | C₂H₅ | 1-benzyl-6-benzyloxy-α-ethyl-4-isopropyl//propionic acid |
| 142 | CH₃ | CH₃ | CH₃ | H | 7-Cl | s | (2-methylthienyl) | CH(CH₃)CH₂CO | C₂H₅ | 8-chloro-β3,3,4,4-pentamethyl-1-(2-thienyl)//propionic acid |
| 143 | C₂H₅ | H | H | H | 5-NO₂ | s | CH₂=CHCH₂ | CH(C₂H₅)₂C(C₂H₅)₂CO | C₂H₅ | 1-methyl-6-nitro-α,α-β,β,3-pentaethyl//propionic acid |
| 144 | C₂H₅ | C₂H₅ | H | H | 5-F | s | CH₃CHCH | CH(C₂H₅)₂CH(CH₃)CO | C₂H₅ | 1-allyl-6-fluoro-α-methyl-β,3,3-triethyl//propionic acid |
| 145 | C₂H₅ | C₂H₅ | H | H | 4-C₂H₅ | s | cyclopropyl | C(n-C₃H₇)CH₂CO | CH₃ | β-propyl-1-(1-propynyl)-3,3,5-triethyl//propionic acid |
| 146 | H | H | H | H | 6-OC₂H₅ | s | phenyl | CH(C₂H₅)CH(C₂H₅)CO | C₂H₅ | 1-cyclopropyl-α,β,β-diethyl-6-ethoxy//propionic acid |
| 147 | CH₃ | CH₃ | CH₃ | H | 6-O-n-C₃H₇ | s | benzyl | C(CH₃)₂CH(CH₃)CO | C₂H₅ | α,β,β,3,3,4,4-heptamethyl-1-phenyl-7-propoxy//propionic acid |
| 148 | C₂H₅ | C₂H₅ | H | H | 5-CH₃ | s | benzyl | C(CH₃)₂C(CH₃)₂CO | C₂H₅ | 1-benzyl-3,3-diethyl-α,α,β,β,6-pentamethyl//propionic acid |

TABLE II-continued

| | | | | | | | | |
|---|---|---|---|---|---|---|---|---|
| 149 | n-C₃H₇ | H | H | 4-OH | S | (2-methylthienyl) | C(CH₃)₂C(CH₂)₃CO | C₂H₅ | 5-hydroxy-3-propyl-α,α,β,β-tetramethyl-1-(2-thienyl)//propionic acid |
| 150 | H | H | H | H | S | C₂H₅ | CH₂CH₂CH₂CO | C₂H₅ | 1-methyl/butyric acid |
| 151 | CH₃ | H | H | H | S | C₂H₅ | CH(CH₃)CH₂CH₂CO | C₂H₅ | γ,3-dimethyl-1-ethyl//butyric acid |
| 152 | CH₃ | CH₃ | H | H | S | n-C₃H₇ | C(C₂H₅)₂CH₂CH₂CO | C₂H₅ | γ,γ-diethyl-3,3-dimethyl-1-propyl//butyric acid |
| 153 | CH₃ | CH₃ | n-C₃H₇ | H | S | CH₂=CH | C(n-C₃H₇)₂CH(n-C₃H₇)CH₂CO | C₂H₅ | 3,3-dimethyl-β,γ,γ,4-tetrapropyl-1-vinyl//butyric acid |
| 154 | H | H | H | H | S | CH₂=CHCH₂ | [C(CH₃)₂]₂CH₂CO | C₂H₅ | 1-allyl-β,β,γ,γ-tetramethyl//butyric acid |
| 155 | H | C₂H₅ | C₂H₅ | 6-Cl | S | CH₂=CH— | [C(C₂H₅)₂]₂CH(C₂H₅)CO | C₂H₅ | 7-chloro-α,β,β,γ,γ,4,4-heptaethyl-1-vinyl//butyric acid |
| 156 | H | CH₃ | CH₃ | 4-CH₃ | S | HC≡CH | [C(CH₃)₂]₃CO | C₂H₅ | 1-ethynyl-α,α,β,β,γ,γ-4,5-octamethyl//butyric acid |
| 157 | C₂H₅ | C₂H₅ | C₂H₅ | 5-OCH₃ (O=) | S | CH₃C≡CH | CH(C₂H₅)[C(C₂H₅)₂]₂CO | C₂H₅ | 6-acetoxy-α,α,β,β,γ,3-3,4-octaethyl-1-(1-propynyl)//butyric acid |
| 158 | H | CH₃ | CH₃ | 7-OCH₃ | S | ☐ | CH₂[C(CH₃)₂]₂CO | C₂H₅ | 1-cyclobutyl-α,α,β,β,-4,4-hexamethyl-8-methoxy//butyric acid |
| 159 | H | H | H | 4-Br | S | ⬠ | CH₂CH(CH₃)CH(CH₃)₂CO | C₂H₅ | 5-bromo-1-cyclopentyl-α,α,β-trimethyl//butyric acid |
| 160 | CH₃ | H | H | 4-n-C₃H₇ | S | △ | CH₂CH₂C(C₂H₅)₂CO | C₂H₅ | 1-cyclopropyl-α,α-diethyl-3,3-dimethyl-5-propyl//butyric acid |
| 161 | H | H | H | 7-C₂H₅ | S | ⬡ | CH₂CH₂CH(CH₃)CO | C₂H₅ | 8-ethyl-α-methyl-1-phenyl//butyric acid |
| 162 | CH₃ | CH₃ | CH₃ | 5-F | S | ⬡ | [CH(CH₃)]₃CO | C₂H₅ | 6-fluoro-α,β,γ,3,3,4-hexamethyl-1-phenyl//butyric acid |
| 163 | CH₃ | CH₃ | H | 4-CH₃ | S | ⬡ | CH(C₂H₅)CH₂CH(C₂H₅)CO | C₂H₅ | α,γ-diethyl-1-phenyl-3,3,5-trimethyl//butyric acid |
| 164 | C₂H₅ | H | H | 6-NO₂ | S | ⬡-CH₂ | [CH(CH₃)]₃CO | C₂H₅ | 1-benzyl-3-ethyl-7-nitro-α,β,γ-trimethyl//butyric acid |

TABLE II-continued

| | | | | | | | |
|---|---|---|---|---|---|---|---|
| 165 | $CH_3$ | $CH_3$ | H | 4-n-$C_3H_7$ | S | [benzene-$CH_2$] | $CH_2[CH(C_2H_5)_2]_2CO$ | $C_2H_5$ | 1-benzyl-α,β-diethyl-3,3-dimethyl-5-propyl//butyric acid |
| 166 | H | H | H | 7-OH | S | [benzene-$CH_2$] | $C(CH_3)_2CH_2C(CH_3)_2CO$ | $C_2H_5$ | 1-benzyl-8-hydroxy-α,α,γ,γ-tetramethyl//butyric acid |
| 167 | $CH_3$ | H | $CH_3$ | 4-$OC_2H_5$ | S | [thienyl] | $[C(CH_3)_3]_3CO$ | $C_2H_5$ | 5-ethoxy-α,α,β,β,γ,γ-3,4-octomethyl-1-(2-thienyl)//butyric acid |
| 168 | $C_2H_5$ | H | $C_2H_5$ | 6-Cl | S | [thienyl] | $CH_3CH_2C(C_2H_5)_2CO$ | $C_2H_5$ | 7-chloro-α,α,3,4,4-pentaethyl-1-(2-thienyl)//butyric acid |

EXAMPLE 169

1-Methyl-1,3,4,9-tetrahydropyrano[3,4-b]indole-1-carboxaldehyde (XI; $R^1 = CH_3$, $R^2$, $R^3$, $R^4$, $R^5$ and $R^6 = H$, and $Y = CO$)

A mixture of the starting material, tryptophol (32.2 g, 0.2 mole), acetonyl acetate (23.2 g, 0.2 mole) and 3.2 g of p-toluenesulfonic acid in 500 ml of benzene is refluxed for 1½ hr. in the presence of a Dean-Stark water trap. The benzene solution is washed with 5% sodium bicarbonate, water, dried and evaporated to afford an oil. The oil is subjected to chromatography on a silica gel column using 10% ethyl acetate in benzene as eluent. The acetate, 1-methyl-1,3,4,9-tetrahydropyrano[3,4-b]indole-1-methanol, acetate is obtained as an oil, nmr(CDCl$_3$) δ 1.52(S,3H), 2.08(S,3H), 4.35(2H).

This acetate is dissolved in 250 ml of methanol and stirred at room temperature. To this solution is added dropwise 20 ml of 10N NaOH. Hydrolysis is immediate. Most of the methanol is removed under reduced pressure, and water is added. The mixture is rendered neutral and extracted with chloroform. The chloroform extract is dried and evaporated to afford the primary alcohol, 1-methyl-1,3,4,9-tetrahydropyrano[3,4-b]indole-1-methanol (X; $R^1 = CH_3$, $R^2$, $R^3$, $R^4$, $R^5$ and $R^6 = H$, $Y = CH_2$ and $R^{17} = H$), m.p. 145°–147° C., nmr(CDCl$_3$) δ 1.43(s,3H), 2.68(t, J = 5.5 cps,2H), 3.65 (d, J = 6 cps, 2H), 3.86 (t, J = 5.5 cps, 2H), after crystallization from benzene-petroleum ether.

N,N-dicyclohexylcarbodiimide (17.36 g, 0.084 mole) is added to a cooled, stirred solution of the above primary alcohol (6.09 g, 0.028 mole) in 63 ml of dimethyl sulfoxidebenzene (2:1) containing trifluoroacetic acid (1.12 ml, 0.014 mole) and pyridine (2.24 ml, 0.028 mole). The reaction is stirred at room temperature under nitrogen for 5 hr. The reaction mixture is now diluted with 600 ml of ether, followed by the dropwise addition of a solution of oxalic acid (7.56 g) in 21 ml of methanol. After 30 minutes, water (600 ml) is added and the insoluble material is collected. The organic phase is washed with water (2X), 5% aqueous sodium bicarbonate (2X) and water (2X). After drying (MgSO$_4$) the organic phase is evaporated to yield an oil. The oil is purified by chromatography on silica gel. Elution with 10% ether in benzene affords the title compound as eluate, nmr (CDCl$_3$) δ 1.59(s,3H), 2.84(t, J = 5.5 cps, 2H), 4.15(t, J = 5.5 cps, 2H).

Oxidation of the latter compound with silver oxide according to the method of Delépine and Bonnet, cited above, affords 1-methyl-1,3,4,9-tetrahydropyrano[3,4-b]indole-1-carboxylic acid, nmr (CDCl$_3$) δ 1.79(s,3H), 2.83(t,2H), 4.17(t,2H), 9.20(1H), identical to the product obtained in Example 4.

By following the procedure of Example 169 but using as starting material an equivalent amount of the appropriate starting material of formula II, for example, those described in Examples 1 to 168, inclusive, instead of tryptophol, and using an equivalent amount of the appropriate ketoalcohol lower alkyl ester of formula VIII, then the acid compounds of formula I in which $R^7$ is hydrogen and Z is hydroxy, for example, the respective products of Examples 1 to 168, inclusive, are obtained.

More specifically exemplified, according to the procedure of Example 169 the use of indole-3-ethanethiol and acetonyl acetate affords 1-methyl-1,3,4,9-tetrahydrothiopyrano[3,4-b]indole-1-acetic acid, identical to the product of Example 3. Similarly, the use of tryptophol and 5-acetoxypentan-2-one affords 1-methyl-1,3,4,9-tetrahydropyrano[3,4-b]indole-1-propionic acid, identical to the product of Example 2.

EXAMPLE 170

N,N,1-trimethyl-1,3,4,9-tetrahydropyrano[3,4-b]indole-1-acetamide (I; $R^1 = CH_3$, $R^2$, $R^3$, $R^4$, $R^5$, $R^6$ and $R^7 = H$, $X = O$, $Y = CH_2CO$ and $Z = N(CH_3)_2$)

To a stirred solution of 1-methyl-1,3,4,9-tetrahydropyrano[3,4-b]indole-1-acetic acid (15 g, 0.061 mole), prepared as described in Example 1, in dry tetrahydrofuran (300 ml), cooled to −5° C, is added triethylamine (18.5 g, 0.183 mole), followed by ethyl chloroformate (16.6 g, 0.153 mole). The mixture is stirred at −5° C for 2 hr. This mixture, which now contains the mixed anhydride of the above starting material, is added dropwise to a cooled 40% aqueous solution of the amine, dimethylamine (225 ml). The resulting mixture is stirred at room temperature for one-half hour. Most of the tetrahydrofuran is evaporated, and the residue partitioned between chloroform and water. The organic phase is washed with water, dried over sodium sulfate, and evaporated under reduced pressure. The residue is subjected to chromatography on silica gel. Elution with 20% ethyl acetate in benzene, followed by crystallization of the eluate from ethyl acetate affords the title compound, m.p. 149°–151° C., $\gamma_{max}^{CHCl_3}$ 3375, 1634 cm$^{-1}$.

In the same manner but replacing dimethylamine with an equivalent amount of ammonium hydroxide (concentrated), methylamine (30% aqueous solution), n-hexylamine (20% aqueous solution), dimethylamine (30% aqueous solution), or aniline (20% aqueous solution), 1-methyl-1,3,4,9-tetrahydropyrano[3,4-b]indole-1-acetamide, m.p. 158°–160° C, N,1-dimethyl-1,3,4,9-tetrahydropyrano[3,4b]indole-1-acetamide, m.p. 138°–140° C, N-(hexyl)-1-methyl-1,3,4,9-tetrahydropyrano[3,4-b]indole-1-acetamide, N,N-diethyl-1-methyl-1,3,4,9-tetrahydropyrano[3,4-b]indole-1-acetamide, m.p. 99° C, and N-phenyl-1-methyl-1,3,4,9-tetrahydropyrano[3,4-b]indole-1-acetamide, m.p. 205°–208° C, are obtained respectively.

By following the procedure of Example 170 but using as a starting material an equivalent amount of one of the acid compounds of formula I, described in Examples 2 to 168, inclusive, instead of 1-methyl-1,3,4,9-tetrahydropyrano[3,4-b]indole-1-acetic acid, and using an equivalent amount of an appropriate amine such as ammonia or a primary or secondary amine described in Example 170, then the corresponding amide compound of formula I

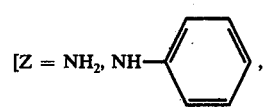

[Z = NH$_2$, NH—⟨phenyl⟩,

NHCH$_3$, N(CH$_3$)$_2$, NH(n-C$_6$H$_{13}$) or N(C$_2$H$_5$)$_2$] is obtained. Examples of such amides are listed as products in Tables III and IV together with the appropriate starting material and amine used for the preparation of the amide. In each case the starting material is noted by the example in which it is prepared.

TABLE III

| EXAMPLE | NO. OF THE EXAMPLE IN WHICH STARTING MATERIAL IS PREPARED | AMINE | PRODUCT: [(PREFIX LISTED BELOW-1,3,4,9-TETRAHYDROPYRANOL[3,4-b]-INDOLE-1-(SUFFIX LISTED BELOW)] PREFIX//SUFFIX |
|---|---|---|---|
| 171 | 2 | $CH_3NH_2$ | N,1-dimethyl//propionamide, m.p. 149–150° C |
| 172 | 2 | $NH_3$ | 1-methyl//propionamide |
| 173 | 2 | $(CH_3)_2NH$ | N,N,1-trimethyl//propionamide |
| 174 | 2 | n-$C_6H_{13}NH_2$ | N-hexyl-1-methyl//propionamide |
| 175 | 2 | $(C_2H_5)_2NH$ | N,N-diethyl-1-methyl//propionamide |
| 176 | 4 | $CH_3NH_2$ | N,1-dimethyl//carboxamide |
| 177 | 4 | $NH_3$ | 1-methyl//carboxamide, m.p. 188–189° C. |
| 178 | 4 | $(CH_3)_2NH$ | N,N,1-trimethyl//carboxamide |
| 179 | 4 | n-$C_6H_{13}NH_2$ | N-hexyl-1-methyl//carboxamide |
| 180 | 4 | $(C_2H_5)_2NH$ | N,N-diethyl-1-methyl//carboxamide |
| 181 | 5 | $CH_3NH_2$ | N,3-dimethyl-1-ethyl//carboxamide |
| 182 | 8 | C₆H₅-NH₂ | 8-ethyl-1-ethynyl-N-phenyl//carboxamide |
| 183 | 9 | $(CH_3)_2NH$ | 1-cyclopropyl-N,N-dimethyl-4-isopropyl//carboxamide |
| 184 | 11 | n-$C_{16}H_{13}NH_2$ | N-hexyl-1-phenyl//carboxamide |
| 185 | 12 | $(C_2H_5)_2NH$ | 1-benzyl-3-methyl-N,N,3-triethyl//carboxamide |
| 186 | 14 | $(CH_3)_2NH$ | N,N,1,4-tetramethyl//acetamide |
| 187 | 15 | $CH_3NH_2$ | 1-ethyl-N-methyl//acetamide |
| 188 | 15 | $NH_3$ | 1-ethyl//acetamide |
| 189 | 15 | $(CH_3)_2NH$ | N,N-dimethyl-1-ethyl//acetamide |
| 190 | 15 | n-$C_{16}H_{13}NH_2$ | 1-ethyl-N-hexyl//acetamide |
| 191 | 15 | $(C_2H_5)_2NH$ | N,N,1-triethyl//acetamide |
| 192 | 16 | $CH_3NH_2$ | N-methyl-1-propyl//acetamide |
| 193 | 16 | $NH_3$ | 1-propyl//acetamide, m.p. 157.5–160° C |
| 194 | 16 | $(CH_3)_2NH$ | N,N-dimethyl-1-propyl//acetamide |
| 195 | 16 | n-$C_6H_{13}NH_2$ | N-hexyl-1-propyl//acetamide |
| 196 | 16 | $(C_2H_5)_2NH$ | N,N-diethyl-1-propyl//acetamide |
| 197 | 17 | $CH_3NH_2$ | 1-isopropyl-N-methyl//acetamide |
| 198 | 17 | $NH_3$ | 1-isopropyl//acetamide |
| 199 | 17 | $(C_2H_5)_2NH$ | N,N-diethyl-1-isopropyl//acetamide |
| 200 | 19 | $CH_3NH_2$ | N,3-dimethyl-1-propyl//acetamide |
| 201 | 19 | C₆H₅-NH₂ | 3-methyl-N-phenyl-1-propyl//acetamide |
| 202 | 19 | $(CH_3)_2NH$ | 1-propyl-N,N,3-trimethyl//acetamide |
| 203 | 19 | n-$C_6H_{13}NH_2$ | N-hexyl-3-methyl-1-propyl//acetamide |
| 204 | 19 | $(C_2H_5)_2NH$ | N,N-diethyl-3-methyl-1-propyl//acetamide |
| 205 | 21 | $CH_3NH_2$ | N,α,1-trimethyl//acetamide |
| 206 | 21 | $NH_3$ | α,1-dimethyl//acetamide |
| 207 | 21 | $(CH_3)_2NH$ | N,N,α,1-tetramethyl//acetamide |
| 208 | 21 | n-$C_6H_{13}NH_2$ | α,1-dimethyl-N-hexyl//acetamide |
| 209 | 21 | $(C_2H_5)_2NH$ | N,N-diethyl-α,1-dimethyl//acetamide |
| 210 | 22 | $CH_3NH_2$ | 1-cyclohexyl-N,α,α-trimethyl//acetamide |
| 211 | 23 | $(C_2H_5)_2NH$ | N,N-diethyl-1-phenyl//acetamide |
| 212 | 26 | $CH_3NH_2$ | N,8-dimethyl-1-propyl//acetamide |
| 213 | 31 | $NH_3$ | 6-benzyloxy-1-methyl//acetamide |
| 214 | 32 | $(CH_3)_2NH$ | 1-propyl-N,N,5-trimethyl//acetamide |
| 215 | 38 | n-$C_6H_{13}NH_2$ | 1-cyclopropyl-α,α-diethyl-3,3-dimethyl-6-ethoxy-N-hexyl//acetamide |
| 216 | 43 | $(CH_3)_2NH$ | 1-benzyl-N,N,α,α,3-pentamethyl-8-propionoxy//acetamide |
| 217 | 46 | $CH_3NH_2$ | 5-iodo-1-isopropyl-N-methyl//propionamide |
| 218 | 49 | $NH_3$ | 1-cyclobutyl-3-methyl-8-nitro-α-propyl//propionamide |
| 219 | 54 | $(CH_3)_2NH$ | 4,4-diethyl-N,N,α,α,β,3-hexamethyl-1-methallyl//propionamide |
| 220 | 57 | $(C_2H_5)_2NH$ | N,N-diethyl-5-methoxy-α-methyl-1-phenyl-3-propyl//propionamide |
| 221 | 62 | $CH_3NH_2$ | N-methyl-β-propyl-1-(1-propynyl)-3,3,5-triethyl//propionamide |
| 222 | 63 | C₆H₅-NH₂ | 1-cyclopropyl-α,β-diethyl-6-ethoxy-N-phenyl//propionamide |
| 223 | 67 | $(CH_3)_2NH$ | N,N,1-trimethyl//butyramide |
| 224 | 67 | $CH_3NH_2$ | N,1-dimethyl//butyramide |
| 225 | 67 | $NH_3$ | 1-methyl//butyramide |
| 226 | 67 | n-$C_6H_{13}NH_2$ | N-hexyl-1-methyl//butyramide |
| 227 | 70 | $CH_3NH_2$ | β,γ,γ,4-tetrapropyl-N,3,3-trimethyl-1-vinyl//butyramide |

TABLE III-continued

| EXAMPLE | NO. OF THE EXAMPLE IN WHICH STARTING MATERIAL IS PREPARED | AMINE | PRODUCT: [(PREFIX LISTED BELOW-1,3,4,9-TETRAHYDROPYRANOL[3,4-b]-INDOLE-1-(SUFFIX LISTED BELOW)] PREFIX/SUFFIX |
|---|---|---|---|
| 228 | 71 | $(C_2H_5)_2NH$ | 1-allyl-N,N-diethyl-$\beta,\beta,\gamma,\gamma$-tetramethyl//butyramide |
| 229 | 73 | $(CH_3)_2NH$ | N,N,$\alpha,\alpha,\beta,\beta,\gamma,\gamma$,4,5-decamethyl-1-ethynyl//butyramide |
| 230 | 76 | $NH_3$ | 5-bromo-1-cyclopentyl-$\alpha,\alpha,\beta$-trimethyl//butyramide |
| 231 | 78 | $CH_3NH_2$ | 8-ethyl-N,$\alpha$-dimethyl-1-phenyl//butyramide |
| 232 | 80 | $(C_2H_5)_2NH$ | 1-phenyl-N,N,$\alpha,\gamma$-tetraethyl-3,3,5-trimethyl//butyramide |
| 233 | 82 | n-$C_6H_{13}NH_2$ | 1-benzyl-$\alpha,\beta$-diethyl-3,3-dimethyl-N-hexyl-5-propyl//butyramide |

TABLE IV

| EXAMPLE | NO. OF THE EXAMPLE IN WHICH STARTING MATERIAL IS PREPARED | AMINE | PRODUCT: [(PREFIX LISTED BELOW-1,3,4,9-TETRAHYDROTRIOPYMIDE-[3,4-b]INDOLE-1-(SUFFIX LISTED BELOW)] PREFIX//SUFFIX |
|---|---|---|---|
| 234 | 3 | $CH_3NH_2$ | N,1-dimethyl//acetamide |
| 235 | 3 | $NH_3$ | 1-methyl//acetamide |
| 236 | 3 | n-$C_6H_{13}NH_2$ | N-hexyl-1-methyl//acetamide |
| 237 | 3 | $(CH_3)_2NH$ | N,N,1-trimethyl//acetamide, m.p. 182–184° C |
| 238 | 3 | $(C_2H_5)_2NH$ | N,N-diethyl-1-methyl//acetamide |
| 239 | 129 | $CH_3NH_2$ | N,1-dimethyl//propionamide |
| 240 | 129 | $NH_3$ | 1-methyl//propionamide |
| 241 | 129 | $(CH_3)_2NH$ | N,N,1-trimethyl//propionamide |
| 242 | 129 | n-$C_6H_{13}NH_2$ | N-hexyl-1-methyl//propionamide |
| 243 | 129 | $(C_2H_5)_2NH$ | N,N-diethyl-1-methyl//propionamide |
| 244 | 87 | $CH_3NH_2$ | N,1-dimethyl//carboxamide |
| 245 | 87 | $NH_3$ | 1-methyl//carboxamide, |
| 246 | 87 | $(CH_3)_2NH$ | N,N,1-trimethyl//carboxamide |
| 247 | 87 | n-$C_6H_{13}NH_2$ | N-hexyl-1-methyl//carboxamide |
| 248 | 87 | $(C_2H_5)_2NH$ | N,N-diethyl-1-methyl//carboxamide |
| 249 | 88 | $CH_3NH_2$ | N,3-dimethyl-1-ethyl//carboxamide |
| 250 | 91 | $NH_3$ | 8-ethyl-1-ethynyl//carboxamide |
| 251 | 92 | $(CH_3)_2NH$ | 1-cyclopropyl-N,N-dimethyl-4-isopropyl//carboxamide |
| 252 | 94 | n-$C_{16}H_{13}NH_2$ | N-hexyl-1-phenyl//carboxamide |
| 253 | 95 | $(C_2H_5)_2NH$ | 1-benzyl-3-methyl-N,N,3-triethyl/carboxamide. |
| 254 | 97 | $(CH_3)_2NH$ | N,N,1,4-tetramethyl//acetamide |
| 255 | 98 | $CH_3NH_2$ | 1-ethyl-N-methyl//acetamide |
| 256 | 98 | $NH_3$ | 1-ethyl//acetamide |
| 257 | 98 | $(CH_3)_2NH$ | N,N-dimethyl-1-ethyl//acetamide |
| 258 | 98 | n-$C_{16}H_{13}NH_2$ | 1-ethyl-N-hexyl//acetamide |
| 259 | 98 | $(C_2H_5)_2NH$ | N,N,1-triethyl//acetamide |
| 260 | 99 | $CH_3NH_2$ | N-methyl-1-propyl//acetamide |
| 261 | 99 | $NH_3$ | 1-propyl//acetamide |
| 262 | 99 | $(CH_3)_2NH$ | N,N-dimethyl-1-propyl//acetamide |
| 263 | 99 | n-$C_6H_{13}NH_2$ | N-hexyl-1-propyl//acetamide |
| 264 | 99 | $(C_2H_5)_2NH$ | N,N-diethyl-1-propyl//acetamide |
| 265 | 100 | $CH_3NH_2$ | 1-isopropyl-N-methyl//acetamide |
| 266 | 100 | $NH_3$ | 1-isopropyl//acetamide |
| 267 | 100 | $(C_2H_5)_2NH$ | N,N-diethyl-1-isopropyl//acetamide |
| 268 | 102 | $CH_3NH_2$ | N,3-dimethyl-1-propyl//acetamide |
| 269 | 102 | $NH_3$ | 3-methyl-1-propyl//acetamide |
| 270 | 102 | $(CH_3)_2NH$ | 1-propyl-N,N,3-trimethyl//acetamide |
| 271 | 102 | n-$C_6H_{13}NH_2$ | N-hexyl-3-methyl-1-propyl//acetamide |
| 272 | 102 | $(C_2H_5)_2NH$ | N,N-diethyl-3-methyl-1-propyl//acetamide |
| 273 | 104 | $CH_3NH_2$ | N,$\alpha$,1-trimethyl//acetamide |
| 274 | 104 | $NH_3$ | $\alpha$,1-dimethyl//acetamide |
| 275 | 104 | $(CH_3)_2NH$ | N,N,$\alpha$,1-tetramethyl//acetamide |
| 276 | 104 | n-$C_6H_{13}NH_2$ | $\alpha$,1-dimethyl-N-hexyl//acetamide |
| 277 | 104 | $(C_2H_5)_2NH$ | N,N-diethyl-$\alpha$,1-dimethyl//acetamide |
| 278 | 105 | $CH_3NH_2$ | 1-cyclohexyl-N,$\alpha,\alpha$-trimethyl//acetamide |
| 279 | 106 | $(C_2H_5)_2NH$ | N,N-diethyl-1-phenyl//acetamide |
| 280 | 109 | $CH_3NH_2$ | N,8-dimethyl-1-propyl//acetamide |
| 281 | 111 | $NH_3$ | 6-bromo-1-propyl//acetamide |
| 282 | 117 | $(CH_3)_2NH$ | $\alpha,\alpha$-diethyl-N,N-dimethyl-8-fluoro-1-vinyl//acetamide |
| 283 | 121 | n-$C_6H_{13}NH_2$ | 1-cyclopropyl-$\alpha,\alpha$-diethyl-3,3-dimethyl-6-ethoxy-N-hexyl//acetamide |
| 284 | 126 | $(CH_3)_2NH$ | 1-benzyl-N,N,$\alpha,\alpha$,3-pentamethyl-8-propionoxy//acetamide |
| 285 | 128 | $CH_3NH_2$ | 1-(2-thienyl)-N,$\alpha,\alpha$-trimethyl//acetamide |
| 286 | 132 | $NH_3$ | 1-cyclobutyl-3-methyl-8-nitro- |

TABLE IV-continued

| EXAMPLE | NO. OF THE EXAMPLE IN WHICH STARTING MATERIAL IS PREPARED | AMINE | PRODUCT: [(PREFIX LISTED BELOW-1,3,4,9-TETRAHYDROTRIOPYMIDE-[3,4-b]INDOLE-1-(SUFFIX LISTED BELOW)] PREFIX//SUFFIX |
|---|---|---|---|
| 287 | 137 | $(CH_3)_2NH$ | α-propyl//propionamide 4,4-diethyl-N,N,α,α,β,3-hexamethyl-1-methallyl//propionamide |
| 288 | 140 | $(C_2H_5)_2NH$ | N,N-diethyl-5-methoxy-α-methyl-1-phenyl-3-propyl//propionamide |
| 289 | 145 | $CH_3NH_2$ | N-methyl-β-propyl-1-(1-propynyl)-3,3,5-triethyl//propionamide |
| 290 | 146 | ⟨phenyl⟩-NH₂ | 1-cyclopropyl-α,β-diethyl-6-ethoxy-N-phenyl//propionamide |
| 291 | 150 | $(CH_3)_2NH$ | N,N,1-trimethyl//butyramide |
| 292 | 150 | $CH_3NH_2$ | N,1-dimethyl//butyramide |
| 293 | 150 | ⟨phenyl⟩-NH₂ | 1-methyl-N-phenyl//butyramide |
| 294 | 150 | $n-C_6H_{13}NH_2$ | N-hexyl-1-methyl//butyramide |
| 295 | 153 | $CH_3NH_2$ | β,γ,γ,4-tetrapropyl-N,3,3-trimethyl-1-vinyl//butyramide |
| 296 | 154 | $(C_2H_5)_2NH$ | 1-allyl-N,N-diethyl-β,β,γ,γ-tetramethyl//butyramide |
| 297 | 155 | $(CH_3)_2NH$ | 7-chloro-N,N-dimethyl-α,β,β,γ,γ,-4,4-heptaethyl-1-ethynyl//butyramide |
| 298 | 159 | $NH_3$ | 5-bromo-1-cyclopentyl-α,α,β-trimethyl//butyramide |
| 299 | 161 | $CH_3NH_2$ | N,α-dimethyl-8-ethyl-1-phenyl//butyramide |
| 300 | 163 | $(C_2H_5)_2NH$ | 1-phenyl-N,N,α,γ-tetraethyl-3,3,5-trimethyl//butyramide |
| 301 | 165 | $n-C_6H_{13}NH_2$ | 1-benzyl-α,β-diethyl-3,3-dimethyl-N-hexyl-5-propyl//butyramide |
| 302 | 168 | $CH_3NH_2$ | 7-chloro-N-methyl-α,α,3,4,4-pentaethyl-1-(2-thienyl)//butyramide |

EXAMPLE 303

1-Methyl-1,3,4,9-tetrahydropyrano[3,4-b]indole-1-carboxamide (I; $R^1 = CH_3$, $R^2$, $R^3$, $R^4$, $R^5$, $R^6$ and $R^7 = H$, X = O, Y = CO and Z = $NH_2$)

By following the procedure of Example 1 but using an equivalent amount of pyruvamide instead of ethyl acetoacetate, 1-methyl-1,3,4,9-tetrahydropyrano[3,4-b]indole-1-carboxamide, m.p. 188°-189° C. after recrystallization from benzene-hexane, identical with the product of Example 177, is obtained.

In the same manner but using an equivalent amount of the appropriate starting material of formula II in place of tryptophol together with the appropriate α, β-, γ- or δ-ketoamide, the products listed in Tables III and IV may be obtained. For example, by using tryptophol (II; $R^2$, $R^3$, $R^4$, $R^5$, $R^6 = H$ and X' = OH) and the β-ketoamide, N,N-dimethyl-acetoacetamide, in the procedure of this Example, N,N-1-trimethyl-1,3,4,9-tetrahydropyrano[3,4-b]indole-1-acetamide, identical with the product of Example 170, is obtained.

EXAMPLE 304

1,9-Dimethyl-1,3,4,9-tetrahydropyrano[3,4-b]indole-1-acetic acid (I; $R^1$, and $R^7 = CH_3$, $R^2$, $R^3$, $R^4$, $R^5$ AND $R^6 = H$, X = O, Y = $CH_2CO$ and Z = CH 1-Methyl-1,3,4,9-tetrahydropyrano[3,4-b]indole-1-acetic acid (10 g., 0.04 mole), prepared as described in Example 1, in 150 ml. of tetrahydrofuran is added dropwise to a stirred suspension of sodium hydride (4,4 g. of 55% dispresion) in 200 ml. of tetrahydrofuran. This mixture is heted at 50° C. with stirring for 2 hr. Methyl iodide (14.2 g. 0.1 mole) is added dropwise and heating and stirring is continued for a further 2 hr.

After cooling, water is added until the solution is clear. The tetrahydrofuran is evaporated off under reduced pressure, the residue is partition between water and benzene. The aqueous phase is washed once with benzene, made acidic with HCl, and extracted with benzene (3x). The organic phase is washed with water, dried over sodium sulfate and treated with charcoal. The organic layer is evaporated. The residue is crystalized from benzene and then ether-petroleum ether to afford the title compound, m.p. 105°-108° C., nmr ($CDCl_3$) δ 1.73 (S,3H), 2.83 (t, J = 5.5, 2H), 3.0 (2H), 3.68 (3), 4.08 (t, J = 5.5, 2H), 7.34 (4H), 9.47 (1H).

In the same manner but replacing methyl iodide with an equivalent amount of ethyl iodide, or propyl iodide 9-ethyl-1-methyl-1,3,4,9-tetrahydropyrano[3,4-b]indole-1-acetic acid, m.p. 134°-136° C., and 1-methyl-9-propyl-1,3,4,9-tetrahydropyrano [3,4-b]indole-1-acetic acid, m.p. 120°-122° C., are obtained, respectively. The corresponding ethyl ester of the latter compound, 1-methyl-9-propyl-1,3,4,9-tetrahydropyrano[3,4-b]indole-1-acetic acid ethyl ester has m.p. 72°-74°C.

By following the procedure of Example 304 but using the starting material an equivalent amount of the acid compounds of formula I, compounds of formula I in which $R^7$ is hydrogen and Z is hydroxy, described in Examples 1 to 168, inclusive, instead of 1-methyl-1,3,4,9-tetrahydropyrano[3,4indole—acetic acid, and using an equivalent amount of an appropriate lower alkyl or lower alkenyl halide, then the corresponding N-alkylated acid compounds of formula I in which $R^7$ is lower alkyl or lower alkenyl are obtained. Examples of these latter compounds are listed as products in Tables V and VI together with the appropriate starting material and alkyl or alkynl halide used for their preparation. In each case the starting material is noted by the Example in which it is prepared.

TABLE V

| EXAMPLE | NO. OF THE EXAMPLE IN WHICH STARTING MATERIAL IS PREPARED | ALKYL OR ALKENYL HALIDE | PRODUCT: [(PREFIX LISTED BELOW-1,3,4,9-TETRAHYDROPYRANO[3,4-b]-INDOLE-1-(SUFFIX LISTED BELOW)] PREFIX//SUFFIX |
|---|---|---|---|
| 305 | 1 | $CH_2=CHCH_2Br$ | 9-allyl-1-methyl//acetic acid, m.p. 103 – 105° C. |
| 306 | 1 | $CH_2=CHBr$ | 1-methyl-9-vinyl//acetic acid |
| 307 | 1 | $CH_2=C(CH_3)CH_2Br$ | 1-methyl-9-methylallyl//acetic acid |
| 308 | 2 | $n-C_3H_7I$ | 1-methyl-9-propyl//propionic acid |
| 309 | 2 | $CH_3I$ | 1,9-dimethyl//propionic acid, m.p. 129–130° C |
| 310 | 2 | $CH_2=CHBr$ | 1-methyl-9-vinyl//propionic acid |
| 311 | 2 | $CH_2=CHCH_2Cl$ | 9-allyl-1-methyl//propionic acid |
| 312 | 4 | $CH_3I$ | 1,9-dimethyl//carboxylic acid |
| 313 | 4 | $CH_2=CHBr$ | 1-methyl-9-vinyl//carboxylic acid |
| 314 | 7 | $CH_3I$ | 6-hydroxy-1-(1-propenyl)-3,3,9-trimethyl//carboxylic acid |
| 315 | 9 | $CH_3CH=CHBr$ | 1-cyclopropyl-4-isopropyl-9-(1-propenyl)//carboxylic acid |
| 316 | 11 | $i-C_3H_7I$ | 9-isopropyl-1-phenyl//carboxylic acid |
| 317 | 15 | $CH_3I$ | 1-ethyl-9-methyl//acetic acid |
| 318 | 15 | $C_2H_5Cl$ | 1,9-diethyl//acetic acid |
| 319 | 15 | $CH_2=CHCH_2Br$ | 9-allyl-1-ethyl//acetic acid |
| 320 | 15 | $CH_2=CHBr$ | 1-ethyl-9-vinyl//acetic acid |
| 321 | 16 | $CH_3I$ | 9-methyl-1-propyl//acetic acid |
| 322 | 16 | $n-C_3H_7Cl$ | 1,9-dipropyl//acetic acid |
| 323 | 16 | $CH_2=CHCH_2Br$ | 9-allyl-1-propyl//acetic acid |
| 324 | 16 | $CH_2=C(CH_3)CH_2Br$ | 9-methallyl-1-propyl//acetic acid |
| 325 | 17 | $CH_3I$ | 9-methyl-1-isopropyl//acetic acid |
| 326 | 17 | $CH_2=CHBr$ | 1-isopropyl-9-vinyl//acetic acid |
| 327 | 19 | $n-C_3H_7Cl$ | 1,9-dipropyl-3-methyl//acetic acid |
| 328 | 19 | $CH_2=CHCH_2Br$ | 9-allyl-3-methyl-1-propyl//acetic acid |
| 329 | 21 | $CH_3I$ | α,1,9-trimethyl//acetic acid |
| 330 | 21 | $CH_2=CHBr$ | α,1-dimethyl-1-vinyl//acetic acid |
| 331 | 22 | $n-C_3H_7Cl$ | 1-cyclohexyl-α,α-dimethyl-9-propyl//acetic acid |
| 332 | 27 | $CH_2=CHCH_2I$ | 9-allyl-1-(2-thienyl)//acetic acid |
| 333 | 29 | $CH_3Cl$ | 1,9-dimethyl-6-methoxy//acetic acid |
| 334 | 34 | $CH_2=CHBr$ | 6-nitro-1-propyl-9-vinyl//acetic acid |
| 335 | 40 | $C_2H_5Cl$ | α,3-dimethyl-9-ethyl-1-phenyl-4,4,5-tripropyl//acetic acid |
| 336 | 42 | $CH_2=CHCH_2Br$ | 9-allyl-1-benzyl-α,α-diisopropyl-3,3,4,4,5-pentaethyl//acetic acid |
| 337 | 48 | $C_2H_5I$ | 7-hydroxy-1-(2-propynyl)-β,β,9-triethyl//propionic acid |
| 338 | 49 | $CH_3I$ | 1-cyclobutyl-3,9-dimethyl-8-nitro-α-propyl//propionic acid |
| 339 | 54 | $CH_2=C(CH_3)CH_2Cl$ | 4,4-diethyl-1,9-dimethallyl-α,α,β,-3-tetramethyl//propionic acid |
| 340 | 59 | $CH_2=CHCH_2Br$ | 9-allyl-8-chloro-β,3,3,4,4-pentamethyl-1-(2-thienyl)//propionic acid |
| 341 | 60 | $CH_2=CHCl$ | 1-methyl-6-nitro-α,α,β,β,3-pentaethyl-9-vinyl//propionic acid |
| 342 | 63 | $C_2H_5Cl$ | 1-cyclopropyl-6-ethoxy-α,β,9-triethyl//propionic acid |
| 343 | 67 | $CH_3I$ | 1,9-dimethyl//butyric acid |
| 344 | 67 | $CH_2=CHCH_2Cl$ | 9-allyl-1-methyl//butyric acid |
| 345 | 68 | $C_2H_5Cl$ | 1,9-diethyl-γ,3-dimethyl//butyric acid |
| 346 | 70 | $CH_2=CHBr$ | 3,3-dimethyl-1,9-divinyl-β,γ,γ,-4-tetrapropyl//butyric acid |
| 347 | 72 | $CH_2=CHBr$ | 7-chloro-1,9-divinyl-α,β,β,γ,γ,-4-heptaethyl//butyric acid |
| 348 | 78 | $C_2H_5I$ | 8,9-diethyl-α-methyl-1-phenyl//butyric acid |
| 349 | 82 | $CH_3I$ | 1-benzyl-α,β-diethyl-5-propyl-3,3,9-trimethyl//butyric acid |
| 350 | 85 | $C_2H_5Br$ | 7-chloro-α,α,3,4,4,9-hexaethyl-1-(2-thienyl)//butyric acid |

TABLE VI

| EXAMPLE | NO. OF THE EXAMPLE IN WHICH STARTING MATERAL IS PREPARED | ALKYL OR ALKENYL HALIDE | PRODUCT: [(PREFIX LISTED BELOW-1,3,-4,9-TETRAHYDROTHIOPYRANO[3,4-b]-INDOLE-1-(SUFFIX LISTED BELOW)] PREFIX//SUFFIX |
|---|---|---|---|
| 351 | 3 | $CH_2=CHCH_2Br$ | 9-allyl-1-methyl//acetic acid |
| 352 | 3 | $CH_3I$ | 1,9-dimethyl//acetic acid |
| 353 | 3 | $CH_2=C(CH_3)CH_2Br$ | 1-methyl-9-methallyl//acetic acid |
| 354 | 129 | $n-C_3H_7I$ | 1-methyl-9-propyl//propionic acid |

TABLE VI-continued

| EXAMPLE | NO. OF THE EXAMPLE IN WHICH STARTING MATERAL IS PREPARED | ALKYL OR ALKENYL HALIDE | PRODUCT: [(PREFIX LISTED BELOW-1,3,-4,9-TETRAHYDROTHIOPYRANO[3,4-b]-INDOLE-1-(SUFFIX LISTED BELOW)] PREFIX//SUFFIX |
|---|---|---|---|
| 355 | 129 | CH$_3$I | 1,9-dimethyl//propionic acid |
| 356 | 129 | CH$_2$=CHBr | 1-methyl-9-vinyl//propionic acid |
| 357 | 129 | CH$_2$=CHCH$_2$Cl | 9-allyl-1-methyl//propionic acid |
| 358 | 87 | CH$_3$I | 1,9-dimethyl//carboxylic acid |
| 359 | 87 | CH$_2$CHBr | 1-methyl-9-vinyl//carboxylic acid |
| 360 | 90 | CH$_3$I | 6-hydroxy-1-(1-propenyl)-3,3,9-trimethyl//carboxylic acid |
| 361 | 92 | CH$_3$CH=CHBr | 1-cyclopropyl-4-isopropyl-9-(1-propenyl)//carboxylic acid |
| 362 | 94 | 2-C$_3$H$_7$I | 9-isopropyl-1-phenyl//carboxylic acid |
| 363 | 98 | CH$_3$I | 1-ethyl-9-methyl//acetic acid |
| 364 | 98 | C$_2$H$_5$Cl | 1,9-diethyl//acetic acid |
| 365 | 98 | CH$_2$=CHCH$_2$Br | 9-allyl-1-ethyl//acetic acid |
| 366 | 98 | CH$_2$=CHBr | 1-ethyl-9-vinyl//acetic acid |
| 367 | 99 | CH$_3$I | 9-methyl-1-propyl//acetic acid |
| 368 | 99 | n-C$_3$H$_7$Cl | 1,9-dipropyl//acetic acid |
| 369 | 99 | CH$_2$=CHCH$_2$Br | 9-allyl-1-propyl//acetic acid |
| 370 | 99 | CH$_2$=C(CH$_3$)CH$_2$Br | 9-methallyl-1-propyl//acetic acid |
| 371 | 100 | CH$_3$I | 9-methyl-1-isopropyl//acetic acid |
| 372 | 100 | CH$_2$=CHBr | 1-isopropyl-9-vinyl//acetic acid |
| 373 | 102 | n-C$_3$H$_7$Cl | 1,9-dipropyl-3-methyl//acetic acid |
| 374 | 102 | CH$_2$=CHCH$_2$Br | 9-allyl-3-methyl-1-propyl//acetic acid |
| 375 | 104 | CH$_3$I | α,1,9-trimethyl//acetic acid |
| 376 | 104 | CH$_2$=CHBr | α,1-dimethyl-1-vinyl//acetic acid |
| 377 | 105 | n-C$_3$H$_7$Cl | 1-cyclohexyl-α,α-dimethyl-9-propyl//acetic acid |
| 378 | 110 | CH$_2$=CHCH$_2$I | 9-allyl-1-(2-thienyl)//acetic acid |
| 379 | 112 | CH$_3$Cl | 1,9-dimethyl-6-methoxy//acetic acid |
| 380 | 117 | CH$_2$=CHBr | α,α-diethyl-1,9-divinyl-8-fluoro//acetic acid |
| 381 | 123 | C$_2$H$_5$Cl | α,3-dimethyl-9-ethyl-1-phenyl-4,4,5-tripropyl//acetic acid |
| 382 | 125 | CH$_2$=CHCH$_2$Br | 9-allyl-1-benzyl-α,α-diisopropyl-3,3,4,4,5-pentaethyl//acetic acid |
| 383 | 131 | C$_2$H$_5$I | 7-hydroxy-1-(2-propynyl)-β,β,9-triethyl//propionic acid |
| 384 | 132 | CH$_3$I | 1-cyclobutyl-3,9-dimethyl-8-nitro-α-propyl//propionic acid |
| 385 | 137 | CH$_2$=C(CH$_3$)CH$_2$Cl | 4,4-diethyl-1,9-dimethallyl-α,α,β,3-tetramethyl//propionic acid |
| 386 | 142 | CH$_2$=CHCH$_2$Br | 9-allyl-8-chloro-β,3,3,4,4-pentamethyl-1-(2-thienyl)//propionic acid |
| 387 | 143 | CH$_2$=CHCl | 1-methyl-6-nitro-α,α,β,β,3-pentaethyl-9-vinyl//propionic acid |
| 388 | 146 | C$_2$H$_5$Cl | 1-cyclopropyl-6-ethoxy-α,β,9-triethyl//propionic acid |
| 389 | 150 | CH$_3$I | 1,9-dimethyl//butyric acid |
| 390 | 150 | CH$_2$=CHCH$_2$Cl | 9-allyl-1-methyl//butyric acid |
| 391 | 151 | C$_2$H$_5$Cl | 1,9-diethyl-γ,3-dimethyl//butyric acid |
| 392 | 153 | CH$_2$=CHBr | 3,3-dimethyl-1,9-divinyl-β,γ,γ,4-tetrapropyl//butyric acid |
| 393 | 155 | CH$_2$=CHBr | 7-chloro-1,9-divinyl-α,β,β,γ,γ,4,4-heptaethyl//butyric acid |
| 394 | 161 | C$_2$H$_5$I | 8,9-diethyl-α-methyl-1-phenyl//butyric acid |
| 395 | 165 | CH$_3$I | 1-benzyl-α,β-diethyl-5-propyl-3,3,9-trimethyl//butyric acid |
| 396 | 168 | C$_2$H$_5$Br | 7-chloro-α,α-3,4,4,9-hexaethyl-1-(2-thienyl)//butyric acid |

EXAMPLE 397

By following the procedure of Example 304 but using as the starting material an equivalent amount of the ester compounds of formula I in which R$^7$ is hydrogen and Z is lower alkoxy, obtained prior to hydrolysis in Example 1 and 3 to 168, inclusive, instead of 1-methyl-1,3,4,9-tetrahydropyrano[3,4-b]indole-1-acetic acid, and using an equivalent amount of an appropriate lower alkyl or lower alkenyl halide, then the corresponding N-alkylated ester compounds of formula I in which R$^7$ is lower alkyl or lower alkenyl, are obtained.

For example, when following the procedure of Example 304, the replacement of 1-methyl-1,3,4,9-tetrahydropyrano[3,4-b]indole-1-acetic acid by an equivalent amount of its corresponding ethyl ester, described in Example 1, and then use the same alkyl halide, methyl iodide, affords 1,9-dimethyl-1,3,4,9-tetrahydropyrano[3,4-b]indole-1-acetic acid ethyl ester.

Similarly, the replacement of 1-methyl-1,3,4,9-tetrahydropyrano[3,4-b]indole-1-acetic acid by an equivalent amount of 1-methyl-1,3,4,9-tetrahydrothiopyrano[3,4-b]indole-1-acetic acid methyl ester, described in Example 3, affords 1,9-dimethyl-1,3,4,9-tetrahydrothiopyrano[3,4-b]indole-1-acetic acid methyl ester.

By following the procedure of Example 170 but using as the starting material an equivalent amount of one of the N-alkylated acid compounds of formula I, described in Examples 304 to 396 inclusive, instead of 1-methyl-1,3,4,9-tetrahydropyrano[3,4-b]indole-1-acetic acid, and using an equivalent amount of an appropriate amine such as ammonia or a primary or secondary amine, described in Example 170, then the corresponding amide compound of formula I in which $R^7$ is lower alkyl or lower alkenyl and Z is amino, lower alkyl amino, di(lower)alkylamino or phenylamino, is obtained. Examples of such amides are listed as products in Tables VII and VIII together with the appropriate starting material, noted by the example in which it is prepared, and the amine used for the preparation of the amide.

TABLE VII

| EXAMPLE | NO. OF THE EXAMPLE IN WHICH STARTING MATERIAL IS PREPARED | AMINE | PRODUCT: [PREFIX LISTED BELOW-1,3,4,9-TETRAHYDROPYRANO[3,4-b]-INDOLE-1-(SUFFIX LISTED BELOW)] PREFIX/SUFFIX |
|---|---|---|---|
| 398 | 304 | $(CH_3)_2NH$ | N,N,1,9-tetramethyl//acetamide, $\nu_{max}^{CHCl_3}$ 1620, 1070 cm$^{-1}$, nmr (CDCl$_3$) δ 1.71, 2.76, 2.89, 3.00, 3.71 |
| 399 | 304 | $CH_3NH_2$ | N,1,9-trimethyl//acetamide, m.p. 136 – 138° C. |
| 400 | 304 | $NH_3$ | 1,9-dimethyl//acetamide, m.p. 105 – 106° C. |
| 401 | 304 | n-$C_6H_{13}NH_2$ | 1,9-dimethyl-N-hexyl//acetamide |
| 402 | 304 | $(C_2H_5)_2NH$ | N,N-diethyl-1,9-dimethyl//acetamide, $\nu_{max}^{CHCl_3}$ 1630 cm$^{-1}$, nmr (CDCl$_3$) δ 1.10, 1.74, 2.80, 3.97 |
| 403 | 305 | $CH_3NH_2$ | 9-allyl-N,1-dimethyl//acetamide |
| 404 | 305 | $(CH_3)_2NH$ | 9-allyl-N,N,1-trimethyl//acetamide |
| 405 | 309 | $CH_3NH_2$ | N,1,9-trimethyl//propionamide, m.p. 148–150° C |
| 405 | 309 | $(C_2H_5)_2NH$ | 1.9-dimethyl-N,N-diethyl//propionamide |
| 407 | 311 | $NH_3$ | 9-allyl-1-methyl//propionamide |
| 408 | 311 | $(CH_3)_2NH$ | 9-allyl-N,N,1-trimethyl//propionamide |
| 409 | 313 | $CH_3NH_2$ | N,1-dimethyl-9-vinyl//carboxamide |
| 410 | 314 | $(C_2H_5)_2NH$ | N,N-diethyl-6-hydroxy-1-(1-propenyl)-3,3,9-trimethyl//carboxamide |
| 411 | 316 | n-$C_6H_3HN_2$ | N-hexyl-9-isopropyl-1-phenyl//carboxamide |
| 412 | 317 | $CH_3HN_2$ | N,9-dimethyl-1-ethyl//acetamide |
| 413 | 319 | $(C_2H_5)_2NH$ | 9-allyl-N,N,1-triethyl//acetamide |
| 414 | 320 | $(CH_3)_2NH$ | N,N-dimethyl-1-ethyl-9-vinyl//acetamide |
| 415 | 321 | $CH_3NH_2$ | N,9-dimethyl-1-propyl//acetamide |
| 416 | 323 | $(C_2H_5)_2NH$ | 9-allyl-N,N-diethyl-1-propyl//acetamide |
| 417 | 331 | $CH_3NH_2$ | 1-cyclohexyl-9-propyl-N,α,α-trimethyl//acetamide |
| 418 | 332 | n-$C_6H_{13}NH_2$ | 9-allyl-N-hexyl-1-(2-thienyl)//acetamide |
| 419 | 333 | $(CH_3)_2NH$ | 6-methoxy-N,N,1,9-tetramethyl//acetamide, m.p. 118–120° C. |
| 420 | 335 | $CH_3NH_2$ | 9-ethyl-1-phenyl-4,4,5-tripropyl-N,α,3-trimethyl//acetamide |
| 421 | 341 | $(C_2H_5)_2NH$ | N,N,α, α, β, β,3-heptaethyl-1-methyl-6-nitro-9-vinyl//propionamide |
| 422 | 342 | $(C_2H_5)_2NH$ | 1-cyclopropyl-6-methoxy-N,N,-α, β,9-pentaethyl-9-vinyl//propionamide |
| 423 | 343 | $CH_3NH_2$ | N,1,9-trimethyl//butyramide |
| 424 | 344 | $(CH_3)_2NH$ | 9-allyl-N,N,1-trimethyl//butyramide |
| 425 | 345 | $NH_3$ | 1,9-diethyl-γ,3-dimethyl//butyramide |
| 426 | 349 | $CH_3NH_2$ | 1-benzyl-α,β-diethyl-5-propyl-N,3,3,9-tetramethyl//butyramide |

TABLE VIII

| EXAMPLE | NO. OF THE EXAMPLE IN WHICH STARTING MATERIAL IS PREPARED | AMINE | PRODUCT:[(PREFIX LISTED BELOW-1,3,4,9-TETRAHYDROTHIOPYRANO[3,4-b]-INDOLE-1-(SUFFIX LISTED BELOW)] PREFIX//SUFFIX |
|---|---|---|---|
| 427 | 352 | $(CH_3)_2NH$ | N,N,1,9-tetramethyl//acetamide, $\nu_{max}^{CHCl_3}$ 1625 cm$^{-1}$, nmr (CDCl$_3$), δ 2.23, 3.65 |

TABLE VIII-continued

| EXAMPLE | NO. OF THE EXAMPLE IN WHICH STARTING MATERIAL IS PREPARED | AMINE | PRODUCT:[(PREFIX LISTED BELOW-1,3,4,9-TETRAHYDROTHIOPYRANO[3,4-b]-INDOLE-1-(SUFFIX LISTED BELOW)] PREFIX//SUFFIX |
|---|---|---|---|
| 428 | 352 | $CH_3NH_2$ | N,1,9-trimethyl//acetamide, m.p. 127–128° C. |
| 429 | 352 | $NH_3$ | 1,9-dimethyl//acetamide |
| 430 | 352 | n-$C_6H_{13}NH_2$ | 1,9-dimethyl-N-hexyl//acetamide |
| 431 | 352 | $(C_2H_5)_2NH$ | N,N-diethyl-1,9-dimethyl//acetamide |
| 432 | 351 | $CH_3NH_2$ | 9-allyl-N,1-dimethyl//acetamide |
| 433 | 351 | $(CH_3)_2NH$ | 9-allyl-N,N,1-trimethyl//acetamide |
| 434 | 355 | $CH_3NH_2$ | N,1,9-trimethyl//propionamide |
| 435 | 355 | $(C_2H_5)_2NH$ | 1,9-dimethyl-N,N-diethyl//propionamide |
| 436 | 357 | $NH_3$ | 9-allyl-1-methyl//propionamide |
| 437 | 357 | $(CH_3)_2NH$ | 9-allyl-N,N,1-trimethyl//propionamide |
| 438 | 359 | $CH_3NH_2$ | N,1-dimethyl-9-vinyl//carboxamide |
| 439 | 360 | $(C_2H_5)_2NH$ | N,N-diethyl-6-hydroxy-1-(1-propenyl)-3,3,9-trimethyl//carboxamide |
| 440 | 362 | n-$C_6H_3NH_2$ | N-hexyl-9-isopropyl-1-phenyl//carboxamide |
| 441 | 363 | $CH_3NH_2$ | N,9-dimethyl-1-ethyl//acetamide |
| 442 | 365 | $(C_2H_5)_2NH$ | 9-allyl-N,N,1-triethyl//acetamide |
| 443 | 366 | $(CH_3)_2NH$ | N,N-dimethyl-1-ethyl-9-vinyl//acetamide |
| 444 | 367 | $CH_3NH_2$ | N,9-dimethyl-1-propyl//acetamide |
| 445 | 369 | $(C_2H_5)_2NH$ | 9-allyl-N,N-diethyl-1-propyl//acetamide |
| 446 | 377 | $CH_3NH_2$ | 1-cyclohexyl-9-propyl-N,α,α-trimethyl//acetamide |
| 447 | 378 | n-$C_6H_{13}NH_2$ | 9-allyl-N-hexyl-1-(2-thienyl)//acetamide |
| 448 | 379 | $(CH_3)_2NH$ | 6-methoxy-N,N,1,9-tetramethyl//acetamide |
| 449 | 381 | $CH_3NH_2$ | 9-ethyl-1-phenyl-4,4,5-tripropyl-N,α,3-trimethyl//acetamide |
| 450 | 387 | $(C_2H_5)_2NH$ | N,N,α,α,β,β,3-heptaethyl-1-methyl-6-nitro-9-vinyl//propionamide |
| 451 | 388 | $(C_2H_5)_2NH$ | 1-cyclopropyl-6-ethoxy-N,N,-α,β,9-pentaethyl//propionamide |
| 452 | 389 | $CH_3NH_2$ | N,1,9-trimethyl//butyramide |
| 453 | 390 | $(CH_3)_2NH$ | 9-allyl-N,N,1-trimethyl//butyramide |
| 454 | 391 | $NH_3$ | 1,9-diethyl-γ,3-dimethyl//butyramide |
| 455 | 395 | $CH_3NH_2$ | 1-benzyl-α,β-diethyl-5-propyl-N,3,3,9-tetramethyl//butyramide |

EXAMPLE 456

6-Hydroxy-1-methyl-1,3,4,9-tetrahydropyrano[3,4-b]indole-1-acetic acid (I; $R^1$ = $Ch_3$, $R^2$, $R^3$, $R^4$, $R^5$ and $R^7$ = H, $R^6$ = 6-OH, X = O, Y = $CH_2CO$ and Z = OH)

A mixture of 6-benzyloxy-1-methyl-1,3,4,9-tetrahydropyrano[3,4-b]indole-1-acetic acid (5.3 g., 0.015 mole), prepared as described in Example 31, in 250 ml. of anhydrous ethanol, and 1.1 g. of 10% palladium on carbon is stirred at room temperature under a hydrogen atmosphere until no more hydrogen is being taken up by the reaction mixture. The catalyst is removed by filtration through diatomaceous earth (Celite) and the filtrate concentrated. The residue is recrystallized from ethanol-benzene to afford the title compound, m.p. 170°–171° C.

The corresponding benzylamine salt is prepared by the mixing of equimolar ethereal solutions of benzylamine and the above product. The resulting solid is recrystallized from acetonitrile to afford 6-hydroxy-1-methyl-1,3,4,9-tetrahydropyrano[3,4-b]indole-1-acetic acid benzylamine salt, m.p. 191°–193° C. The corresponding acetate is prepared by allowing a mixture of the title compound and a five molar excess of acetic anhydride in pyridine solution to stand for 24 hr. Dilution of the mixture with water extraction with ether and recrystallization of the extract residue from benzene-petroleum ether, affords 6-acetoxy-1-methyl-1,3,4,9-tetrahydro[3,4-b]indole-1-acetic acid, identical with the product of Example 30.

Table IX provides further examples of the compounds of this invention. The remarks relating to procedure, starting material and product applied to Table I are applicable also to Table IX. Note also that starting materials of both formulae II and IIa are utilized.

TABLE IX

| | STARTING MATERIAL OF FORMULA IIa | | | | | | KETOESTER OF FORMULA VI $(R^1-\overset{\overset{O}{\|}}{C}-Y-OR^{16})$ | | | PRODUCT: [(PREFIX LISTED BELOW)-1,3,4,9-TETRAHYDROPYRANO-[3,4-b]INDOLE-1-(SUFFIX LISTED BELOW)] |
|---|---|---|---|---|---|---|---|---|---|---|
| EXAMPLE | $R^2$ | $R^3$ | $R^4$ | $R^5$ | $R^6$ | X | $R^1$ | Y | $R^{16}$ | PREFIX//SUFFIX |
| 457 | H | H | CH$_3$ | H | H | O | n-C$_3$H$_7$ | CH$_2$CO | C$_2$H$_5$ | 4-methyl-1-propyl//acetic acid, m.p. 191 – 195° C. |
| 458 | H | H | H | H | 5-CH$_3$ | O | n-C$_3$H$_7$ | CH$_2$CO | C$_2$H$_5$ | 6-methyl-1-propyl//acetic acid, m.p. 126 – 129° C. |
| 459 | H | H | H | H | 4-i-C$_3$H$_7$ | O | n-C$_3$H$_7$ | CH$_2$CO | C$_2$H$_5$ | 5-isopropyl-1-propyl//acetic acid, m.p. 164.5 – 165° C. |
| 460 | H | H | H | H | 4-Cl | O | n-C$_3$H$_7$ | CH$_2$CO | C$_2$H$_5$ | 5-chloro-1-propyl//acetic acid, m.p. 166 – 169° C. |
| 461 | H | H | H | H | 6-OCH$_3$ | O | n-C$_3$H$_7$ | CH$_2$CO | C$_2$H$_5$ | 7-methoxy-1-propyl//acetic acid, m.p. 164 – 166° C. |
| 462 | H | H | CH$_3$ | H | H | O | C$_2$H$_5$ | CH$_2$CO | C$_2$H$_5$ | 1-ethyl-4-methyl//acetic acid, m.p. 153 – 156° C., (Isomer A), m.p. 132 – 133° C (Isomer B) |
| 463 | H | H | H | H | 4-Cl | O | CH$_3$ | CH$_2$CO | C$_2$H$_5$ | 5-chloro-1-methyl//acetic acid, m.p. 183 – 184° C. |
| 464 | H | H | H | H | 4-C$_2$H$_5$ | O | n-C$_3$H$_7$ | CH$_2$CO | C$_2$H$_5$ | 5-ethyl-1-propyl//acetic acid, m.p. 130 – 131° C. |
| 465 | H | CH$_3$ | H | H | H | O | C$_2$H$_5$ | CH$_2$CO | C$_2$H$_5$ | 1-ethyl-3-methyl//acetic acid, m.p. 147 – 148° C., (Isomer A), m.p. 145 – 147° C., (Isomer B) |
| 466 | H | H | H | H | 4-CH$_3$ | O | C$_2$H$_5$ | CH$_2$CO | C$_2$H$_5$ | 1-ethyl-5-methyl//acetic acid, m.p. 170 – 172° C. |
| 467 | H | H | H | H | 4-CH$_3$ | O | CH$_3$ | CH$_2$CO | C$_2$H$_5$ | 1,5-dimethyl//acetic acid, m.p. 150 – 151° C. |
| 468 | H | H | H | H | 4-Cl | O | C$_2$H$_5$ | CH$_2$CO | C$_2$H$_5$ | 5-chloro-1-ethyl//acetic acid, m.p. 154 – 157° C. |
| 469 | H | H | CH$_3$ | H | H | O | t-C$_4$H$_9$ | CH$_2$CO | C$_2$H$_5$ | 1-t-butyl-4-methyl//acetic acid, m.p. 179 – 181° C. |
| 470 | H | H | H | H | 4-OCH$_3$ | O | n-C$_3$H$_7$ | CH$_2$CO | C$_2$H$_5$ | 5-methoxy-1-propyl//acetic acid, m.p. 148 – 151° C. |
| 471 | H | H | H | H | 7-CH$_3$ | O | C$_2$H$_5$ | CH$_2$CO | C$_2$H$_5$ | 1-ethyl-8-methyl//acetic acid, m.p. 160 – 161° C. |
| 472 | H | H | CH$_3$ | H | 7-CH$_3$ | O | C$_2$H$_5$ | CH$_2$CO | C$_2$H$_5$ | 4,8-dimethyl-1-ethyl//acetic acid, m.p. 129 – 131° C. |
| 473 | H | H | CH$_3$ | H | 7-CH$_3$ | O | CH$_3$ | CH$_2$CO | C$_2$H$_5$ | 1,4,8-trimethyl// 157 – 159° C. |
| 474 | H | H | H | H | 7-Cl | O | C$_2$H$_5$ | CH$_2$CO | C$_2$H$_5$ | 8-chloro-1-ethyl//acetic acid, m.p. 168 – 171° C. |
| 475 | H | H | H | H | 6-Cl | O | C$_2$H$_5$ | CH$_2$CO | C$_2$H$_5$ | 7-chloro-1-ethyl//acetic acid, m.p. 182 – 183° C. |
| 476 | H | H | H | H | 6-Cl | O | n-C$_3$H$_7$ | CH$_2$CO | C$_2$H$_5$ | 7-chloro-1-propyl//acetic acid, m.p. 182 – 183° C. |
| 477 | H | H | H | H | 7-C$_2$H$_5$ | O | C$_2$H$_5$ | CH$_2$CO | C$_2$H$_5$ | 1,8-diethyl//acetic acid, m.p. 145 – 148° C |
| 478 | H | H | H | H | 7-OCH$_3$ | O | C$_2$H$_5$ | CH$_2$CO | C$_2$H$_5$ | 1-ethyl-8-methoxy//acetic acid, m.p. 132° C. |
| 479 | H | H | H | H | 4-CH$_3$, 7-CH$_3$ | O | C$_2$H$_5$ | CH$_2$CO | C$_2$H$_5$ | 5,8-dimethyl-1-ethyl//acetic acid, m.p. 175 – 176° C |
| 480 | H | H | H | H | 4-Cl, 7-Cl | O | C$_2$H$_5$ | CH$_2$CO | C$_2$H$_5$ | 5,8-dichloro-1-ethyl//acetic acid, m.p. 168 – 169° C |
| 481 | H | H | H | H | 6-Cl, 7-Cl | O | n-C$_3$H$_7$ | CH$_2$CO | C$_2$H$_5$ | 7,8-dichloro-1-propyl acetic acid |
| 482 | H | H | H | H | 4-Cl, 6-Cl | O | CH$_3$ | CH$_2$CO | C$_2$H$_5$ | 5,7-dichloro-1-methyl acetic acid |
| 483 | H | H | H | H | 4-CH$_3$, 7-Cl | O | C$_2$H$_5$ | CH$_2$CO | C$_2$H$_5$ | 8-chloro-1-ethyl-5-methyl/acetic acid |
| 484 | H | H | H | H | 4-Cl, 7-CH$_3$ | O | C$_2$H$_5$ | CH$_2$CO | C$_2$H$_5$ | 5-chloro-1-ethyl-8-methyl//acetic acid |
| 485 | H | H | CH$_3$ | H | 4-C$_2$H$_5$ | O | C$_2$H$_5$ | CH$_2$CO | C$_2$H$_5$ | 7-bromo-1,5-diethyl- |

TABLE IX-continued

| EXAMPLE | STARTING MATERIAL OF FORMULA IIa | | | | | KETOESTER OF FORMULA VI $(R^1-\overset{\overset{O}{\|}}{C}-Y-OR^{16})$ | | | | PRODUCT: [(PREFIX LISTED BELOW)-1,3,4,9-TETRAHYDROPYRANO-[3,4-b]INDOLE-1-(SUFFIX LISTED BELOW)] |
|---|---|---|---|---|---|---|---|---|---|---|
| | $R^2$ | $R^3$ | $R^4$ | $R^5$ | $R^6$ | X | $R^1$ | Y | $R^{16}$ | PREFIX//SUFFIX |
| | | | | | 6-Br | | | | | 4-methyl//acetic acid |
| 486 | H | H | H | H | 6-Cl<br>7-CH$_3$ | O | CH$_3$ | CH$_2$CO | C$_2$H$_5$ | 7-chloro-1,8-dimethyl acetic acid |
| 487 | H | H | CH$_3$ | H | 4-Cl<br>6-Cl<br>7-Cl | O | CH$_3$ | CH$_2$CO | C$_2$H$_5$ | 1,4-dimethyl-5,7,8-trichloro//acetic acid |
| 488 | H | H | H | H | 4-OCH$_3$<br>5-OCH$_3$<br>6-OCH$_3$<br>7-OCH$_3$ | O | n-C$_3$H$_7$ | CH$_2$CO | C$_2$H$_5$ | 1-propyl-5,6,7,8-tetramethoxy//acetic acid |
| 489 | H | H | H | H | 4-OCH$_3$<br>7-Cl | O | C$_2$H$_5$ | CH$_2$CO | C$_2$H$_5$ | 8-chloro-1-ethyl-5-methoxy//acetic acid |
| 490 | H | H | CH$_3$ | H | 4-OCH$_3$<br>6-Cl<br>7-Cl | O | CH$_3$ | CH$_2$CO | C$_2$H$_5$ | 7,8-dichloro-1-methyl-5-methoxy//acetic acid |
| 491 | H | H | H | H | 4-OCH$_3$<br>7-OCH$_3$ | O | C$_2$H$_5$ | CH$_2$CO | C$_2$H$_5$ | 1-ethyl-5,8-dimethoxy//acetic acid m.p. 167 - 169° C. |
| 492 | CH$_3$ | H | H | H | 4-F<br>7-Cl | O | n-C$_3$H$_7$ | CH$_2$CO | C$_2$H$_5$ | 8-chloro-5-fluoro-3-methyl-1-propyl//acetic acid |
| 493 | H | H | H | H | 4-F<br>6-Cl<br>7-Cl | O | C$_2$H$_5$ | CH$_2$CO | C$_2$H$_5$ | 7,8-dichloro-5-fluoro-1-ethyl//acetic acid |
| 494 | C$_2$H$_5$ | H | CH$_3$ | H | 4-CF$_3$<br>7-CH$_3$ | O | CH$_3$ | CH$_2$CO | C$_2$H$_5$ | 3-ethyl-5-trifluoromethyl-1,4,8-trimethyl//acetic acid |
| 495 | H | H | H | H | 6-CF$_3$ | O | C$_2$H$_5$ | CH$_2$CO | C$_2$H$_5$ | 1-ethyl-7-trifluoromethyl//acetic acid, m.p. 185 - 187° C |
| 496 | H | H | CH$_3$ | H | 7-CF$_3$ | O | C$_2$H$_5$ | CH$_2$CO | C$_2$H$_5$ | 1-ethyl-4-methyl-8-trifluoromethyl//acetic acid |
| 497 | H | H | C$_2$H$_5$ | H | 5-CH$_3$<br>7-NO$_2$ | O | CH$_3$ | CH$_2$CO | C$_2$H$_5$ | 1,6-dimethyl-4-ethyl-8-nitro//acetic acid |
| 498 | CH$_3$ | H | H | H | 4-NO$_2$<br>7-Cl | O | n-C$_3$H$_7$ | CH$_2$CO | C$_2$H$_5$ | 8-chloro-3-methyl-5-nitro-1-propyl//acetic acid |
| 499 | H | H | H | H | 5-SH | O | CH$_3$ | CH$_2$CO | C$_2$H$_5$ | 6-mercapto-1-methyl//acetic acid |
| 500 | H | H | CH$_3$ | H | 7-SCH$_3$ | O | CH$_3$ | CH$_2$—CH$_2$CO | C$_2$H$_5$ | 1,4-dimethyl-8-methylthio//propionic acid |
| 501 | H | H | H | H | 6-SC$_2$H$_5$ | O | C$_2$H$_5$ | CH$_2$CO | C$_2$H$_5$ | 1-ethyl-7-ethylthio//acetic acid |
| 502 | H | H | H | H | 4-NH$_2$ | O | C$_2$H$_5$ | CH$_2$CO | C$_2$H$_5$ | 5-amino-1-ethyl//acetic acid |
| 503 | H | H | H | H | 6-NH$_2$ | O | C$_2$H$_5$ | CH$_2$CO | C$_2$H$_5$ | 7-amino-1-ethyl//acetic acid |
| 504 | H | H | H | H | 4-SO$_2$NH$_2$ | O | n-C$_3$H$_7$ | CH$_2$CO | C$_2$H$_5$ | 1-propyl-5-sulfamoyl//acetic acid |
| 505 | H | H | H | H | 6-SO$_2$HN$_2$ | O | CH$_3$ | CH$_2$CO | C$_2$H$_5$ | 1-methyl-7-sulfamoyl//acetic acid |
| 506 | H | H | H | H | H | O | ▷ (cyclopropyl) | CH$_2$CO | C$_2$H$_5$ | 1-cyclopropyl//acetic acid, m.p. 128 - 129° C |
| 507 | H | H | H | H | H | O | C$_6$H$_5$-CH$_2$ | CH$_2$CO | C$_2$H$_5$ | 1-benzyl//acetic acid, m.p. 139 - 141° C |
| 508 | H | H | H | H | 5-F | O | C$_2$H$_5$ | CH$_2$CO | C$_2$H$_5$ | 1-ethyl-6-fluoro//acetic acid, m.p. 125 - 126° C |
| 509 | H | H | CH$_3$ | H | 6-Cl | O | C$_2$H$_5$ | CH$_2$CO | C$_2$H$_5$ | 7-chloro-1-ethyl-4-methyl//acetic acid m.p. 141 - 143° C |
| 510 | H | H | H | H | 6-F | O | C$_2$H$_5$ | CH$_2$CO | C$_2$H$_5$ | 1-ethyl-7-fluoro//acetic acid, m.p. 164 - 166° C |
| 511 | H | H | CH$_3$ | H | 7-Cl | O | C$_2$H$_5$ | CH$_2$CO | C$_2$H$_5$ | 8-chloro-1-ethyl-4-methyl//acetic acid, m.p. 157 - 163° C |
| 512 | H | H | CH$_3$ | H | 7-C$_2$H$_5$ | O | C$_2$H$_5$ | CH$_2$CO | C$_2$H$_5$ | 1,8-diethyl-4-methyl//acetic acid, m.p. 125 - 130° C |
| 513 | H | H | H | H | 7-n-C$_3$H$_7$ | O | C$_2$H$_5$ | CH$_2$CO | C$_2$H$_5$ | 1-ethyl-8-propyl//acetic acid, m.p. 111 - 114° C |
| 514 | H | H | H | H | 7-(CH$_3$)$_2$—CH | O | C$_2$H$_5$ | CH$_2$CO | C$_2$H$_5$ | 1-ethyl-8-isopropyl//acetic acid; m.p. 165 - 167° C |
| 515 | H | H | H | H | 7-n-C$_4$H$_9$ | O | C$_2$H$_5$ | CH$_2$CO | C$_2$H$_5$ | 8-butyl-1-ethyl//acetic acid, nmr (CDCl$_3$) δ 1.0 (t, |

TABLE IX-continued

| EXAMPLE | STARTING MATERIAL OF FORMULA IIa | | | | | X | KETOESTER OF FORMULA VI $R^1-\overset{O}{\underset{\|}{C}}-Y-OR^{16}$ | | | PRODUCT: [(PREFIX LISTED BELOW)-1,3,4,9-TETRAHYDROPYRANO-[3,4-b]INDOLE-1-(SUFFIX LISTED BELOW)] |
|---|---|---|---|---|---|---|---|---|---|---|
| | $R^2$ | $R^3$ | $R^4$ | $R^5$ | $R^6$ | | $R^1$ | Y | $R^{16}$ | PREFIX//SUFFIX |
| | | | | | | | | | | J=7,6H), 6.9-7.11 (m,3H) |
| 516 | H | H | H | H | 7-sec-$C_4H_9$ | O | $C_2H_5$ | $CH_2CO$ | $C_2H_5$ | 8-sec-butyl-1-ethyl//acetic acid, m.p. 135 – 137° C |
| 517 | H | H | H | H | 7-$(CH_3)_2$—$CHCH_2$ | O | $C_2H_5$ | $CH_2CO$ | $C_2H_5$ | 1-ethyl-8-isobutyl// δ 0.9 (m,9H), 7.0-7.5 (m,3H) |
| 518 | H | H | H | H | 7-tert-$C_4H_9$ | O | $C_2H_5$ | $CH_2CO$ | $C_2H_5$ | 8-tert-butyl-1-ethyl//acetic acid, m.p. 169 – 170° C |
| 519 | H | H | $CH_3$ | H | {4-$CH_3$, 7-$CH_3$} | O | $C_2H_5$ | $CH_2CO$ | $C_2H_5$ | 1-ethyl-4,5,8-trimethyl//acetic acid, m.p. ≈168° C |
| 520 | H | H | H | H | {6-Cl, 7-Cl} | O | $C_2H_5$ | $CH_2CO$ | $C_2H_5$ | 7,8-dichloro-1-ethyl//acetic acid, m.p. 112 – 117° C |
| 521 | H | H | H | H | {6-$CH_3$, 7-Cl} | O | $C_2H_5$ | $CH_2CO$ | $C_2H_5$ | 8-chloro-1-ethyl-7-methyl//acetic acid, m.p. 117 – 120° C |
| 522 | H | H | H | H | {6-Cl, 7-$CH_3$} | O | $C_2H_5$ | $CH_2CO$ | $C_2H_5$ | 7-chloro-1-ethyl-8-methyl//acetic acid, m.p. 119 – 123° C |
| 523 | H | H | H | H | {6-F, 7-$CH_3$} | O | $C_2H_5$ | $CH_2CO$ | $C_2H_5$ | 1-ethyl-7-fluoro-8-methyl//acetic acid, m.p. 158 – 160° C |
| 524 | H | H | H | H | 7-$C_2H_5$ | O | n-$C_3H_7$ | $CH_2CO$ | $C_2H_5$ | 8-ethyl-1-propyl//acetic acid, m.p. 103 – 105° C |
| 525 | H | H | H | H | 7-n-$C_3H_7$ | O | n-$C_3H_7$ | $CH_2CO$ | $C_2H_5$ | 1,8-dipropyl//acetic acid, m.p. 109° C |
| 526 | H | H | H | H | {6-Cl, 7-$CH_3$} | O | n-$C_3H_7$ | $CH_2CO$ | $C_2H_5$ | 7-chloro-8-methyl-1-propyl//acetic acid m.p. 156 – 158° C |
| 527 | H | H | H | H | 5-cyclopropyl | O | $C_2H_5$ | $CH_2CO$ | $C_2H_5$ | 8-cyclopropyl-1-ethyl//acetic acid, m.p. 153 – 154° C |
| 528 | H | H | H | H | 5-cyclopentyl | O | $C_2H_5$ | $CH_2CO$ | $C_2H_5$ | 8-cyclopentyl-1-ethyl//acetic acid, m.p. 137 – 139° C |
| 529 | H | H | H | H | 5-cyclohexyl | O | $C_2H_5$ | $CH_2CO$ | $C_2H_5$ | 8-cyclohexyl-1-ethyl//acetic acid, m.p. 156 – 159° C |
| 530 | H | H | H | H | 5-phenyl | O | $C_2H_5$ | $CH_2CO$ | $C_2H_5$ | 1-ethyl-8-phenyl//acetic acid, m.p. 184-187° C |

We claim:

1. 1-Cyclopropyl-1,3,4,9-tetrahydropyrano[3,4-b]indole-1-acetic acid.
2. 1-Benzyl-1,3,4,9-tetrahydropyrano[3,4-b]indole-1-acetic acid.
3. 1-Ethyl-6-fluoro-1,3,4,9-tetrahydropyrano[3,4-b]indole-1-acetic acid.
4. 7-Chloro-1-ethyl-4-methyl-1,3,4,9-tetrahydropyrano[3,4-b]indole-1-acetic acid.
5. 1-Ethyl-7-fluoro-1,3,4,9-tetrahydropyrano[3,4-b]indole-1-acetic acid.
6. 8-Chloro-1-ethyl-4-methyl-1,3,4,9-tetrahydropyrano[3,4-b]indole-1-acetic acid.
7. 1,8-Diethyl-4-methyl-1,3,4,9-tetrahydropyrano[3,4-b]indole-1-acetic acid.
8. 1-Ethyl-8-propyl-1,3,4,9-tetrahydropyrano[3,4-b]indole-1-actic acid.
9. 1-Ethyl-8-isopropyl-1,3,4,9-tetrahydropyrano[3,4-b]indole1-acetic acid.
10. 8-Butyl-1-ethyl-1,3,4,9-tetrahydropyrano[3,4-b]indole-1-acetic acid.
11. 8-sec-Butyl-1-ethyl-1,3,4,9-tetrahydropyrano[3,4-b]indole-1-acetic acid.
12. 1-Ethyl-8-isobutyl-1,3,4,9-tetrahydropyrano[3,4-b]indole-1-acetic acid.
13. 8-tert-Butyl-1-ethyl-1,3,4,9-tetrahydropyrano[3,4-b]indole-1-acetic acid.
14. 1-Ethyl-4,5,8-trimethyl-1,3,4,9-tetrahydropyrano[3,4-b]indole-1-acetic acid.
15. 7,8-Dichloro-1-ethyl-1,3,4,9-tetrahydropyrano[3,4-b]indole-1-acetic acid.
16. 8-Chloro-1-ethyl-7-methyl-1,3,4,9-tetrahydropyrano[3,4-b]indole-1-acetic acid.
17. 7-Chloro-1-ethyl-8-methyl-1,3,4,9-tetrahydropyrano[3,4-b]indole-1-acetic acid.
18. 1-Ethyl-7-fluoro-8-methyl-1,3,4,9-tetrahydropyrano[3,4-b]indole-1-acetic acid.
19. 8-Ethyl-1-propyl-1,3,4,9-tetrahydropyrano[3,4-b]indole-1-acetic acid.
20. 1,8-Dipropyl-1,3,4,9-tetrahydropyrano[3,4-b]indole-1-acetic acid.
21. 7-Chloro-8-methyl-1-propyl-1,3,4,9-tetrahydropyrano[3,4-b]indole-1-acetic acid.

* * * * *